United States Patent
Jaffe et al.

(10) Patent No.: US 9,103,528 B2
(45) Date of Patent: Aug. 11, 2015

(54) SOLID STATE CONTINUOUS WHITE LIGHT SOURCE

(71) Applicant: Lumencor, Inc., Beaverton, OR (US)

(72) Inventors: Steven M. Jaffe, Portland, OR (US);
Claudia B. Jaffe, Portland, OR (US);
George S. Tylinski, Portland, OR (US)

(73) Assignee: LUMENCOR, INC, Beaverton, OR (US)

( * ) Notice: Subject to any disclaimer, the term of this patent is extended or adjusted under 35 U.S.C. 154(b) by 250 days.

(21) Appl. No.: 13/741,480

(22) Filed: Jan. 15, 2013

(65) Prior Publication Data

US 2013/0188384 A1    Jul. 25, 2013

Related U.S. Application Data

(60) Provisional application No. 61/644,921, filed on May 9, 2012, provisional application No. 61/589,086, filed on Jan. 20, 2012.

(51) Int. Cl.
*F21V 7/04*     (2006.01)
*F21V 9/16*     (2006.01)
(Continued)

(52) U.S. Cl.
CPC ............... *F21V 9/16* (2013.01); *A61B 1/0646* (2013.01); *A61B 1/0669* (2013.01); *A61B 1/0684* (2013.01); *F21V 7/00* (2013.01); *F21V 9/083* (2013.01); *F21V 29/02* (2013.01); *F21V 29/20* (2013.01); *G02B 6/0001* (2013.01); *G02B 6/0003* (2013.01); *G02B 6/0006* (2013.01);
(Continued)

(58) Field of Classification Search
CPC .......................................................... F21V 9/16
USPC .......................................................... 362/555
See application file for complete search history.

(56) References Cited

U.S. PATENT DOCUMENTS

| | | | |
|---|---|---|---|
| 1,998,054 | A | 4/1935 | McBurney |
| 3,313,337 | A | 4/1967 | Bernat |

(Continued)

FOREIGN PATENT DOCUMENTS

| | | |
|---|---|---|
| CA | 2 280 398 | 4/2000 |
| EP | 1 426 807 | 12/2003 |

(Continued)

OTHER PUBLICATIONS

International Search Report dated Jun. 3, 2013 for PCT/US2013/029931, 11 pages.

(Continued)

*Primary Examiner* — Anh Mai
*Assistant Examiner* — Hana Featherly
(74) *Attorney, Agent, or Firm* — Tucker Ellis LLP

(57) ABSTRACT

A solid state illumination system is provided as a replacement for conventional arc light, metal halide and Xenon white-light sources for applications in life sciences including, microscopy, fluorescence microscopy, and endoscopy. The solid state illumination system generates high quality white light output from LED light sources. The white light output is continuous in the visible spectrum from 380 nm to 650 nm and is suitable for imaging all the most common fluorophores and fluorescent proteins. In embodiments, an LED light pipe engine is used to generate a portion of the spectral content of the white light output. In alternative embodiments the solid state illumination system produces light output of a selectable color.

20 Claims, 20 Drawing Sheets

(51) Int. Cl.

| | |
|---|---|
| F21V 9/08 | (2006.01) |
| F21V 29/00 | (2015.01) |
| F21V 8/00 | (2006.01) |
| F21V 7/00 | (2006.01) |
| F21V 29/02 | (2006.01) |
| G02B 21/16 | (2006.01) |
| G02B 27/14 | (2006.01) |
| A61B 1/06 | (2006.01) |
| G02B 6/42 | (2006.01) |

(52) U.S. Cl.
CPC ............. *G02B 21/16* (2013.01); *G02B 27/141* (2013.01); *G02B 6/4296* (2013.01)

(56) References Cited

U.S. PATENT DOCUMENTS

| | | |
|---|---|---|
| 3,637,285 A | 1/1972 | Stewart |
| 3,759,604 A | 9/1973 | Thelen |
| 3,881,800 A | 5/1975 | Friesem |
| 3,982,151 A | 9/1976 | Ludovici |
| 4,003,080 A | 1/1977 | Maiman |
| 4,298,820 A | 11/1981 | Bongers |
| 4,371,897 A | 2/1983 | Kramer |
| 4,510,555 A | 4/1985 | Mori |
| 4,539,687 A | 9/1985 | Gordon |
| 4,602,281 A | 7/1986 | Nagasaki et al. |
| 4,626,068 A | 12/1986 | Caldwell |
| 4,642,695 A | 2/1987 | Iwasaki |
| 4,644,141 A | 2/1987 | Hagen et al. |
| 4,657,013 A | 4/1987 | Hoerenz et al. |
| 4,695,332 A | 9/1987 | Gordon |
| 4,695,732 A | 9/1987 | Ward |
| 4,695,762 A | 9/1987 | Berkstresser |
| 4,713,577 A | 12/1987 | Gualtieri |
| 4,724,356 A | 2/1988 | Daehler |
| 4,798,994 A | 1/1989 | Rijpers |
| 4,804,850 A | 2/1989 | Norrish et al. |
| 4,852,985 A | 8/1989 | Fujihara et al. |
| 4,937,661 A | 6/1990 | Van Der Voort |
| 4,995,043 A | 2/1991 | Kuwata |
| 5,052,016 A | 9/1991 | Mahbobzadeh |
| 5,089,860 A | 2/1992 | Deppe |
| 5,109,463 A | 4/1992 | Lee |
| 5,126,626 A | 6/1992 | Iwasaki |
| 5,128,846 A | 7/1992 | Mills et al. |
| 5,137,598 A | 8/1992 | Thomas |
| 5,193,015 A | 3/1993 | Shanks |
| 5,200,861 A | 4/1993 | Moskovich |
| 5,226,053 A | 7/1993 | Cho |
| 5,231,533 A | 7/1993 | Gonokami |
| 5,233,372 A | 8/1993 | Matsumoto |
| 5,249,195 A | 9/1993 | Feldman |
| 5,285,131 A | 2/1994 | Muller |
| 5,289,018 A | 2/1994 | Okuda |
| 5,312,535 A | 5/1994 | Waska |
| 5,315,128 A | 5/1994 | Hunt |
| 5,332,892 A | 7/1994 | Li et al. |
| 5,345,333 A | 9/1994 | Greenberg |
| 5,363,398 A | 11/1994 | Glass |
| 5,416,342 A | 5/1995 | Edmond et al. |
| 5,416,617 A | 5/1995 | Loiseaux |
| 5,418,584 A | 5/1995 | Larson |
| 5,428,476 A | 6/1995 | Jensen |
| 5,469,018 A | 11/1995 | Jacobsen |
| 5,475,281 A | 12/1995 | Heijboer |
| 5,478,658 A | 12/1995 | Dodabalapur |
| 5,489,771 A | 2/1996 | Beach et al. |
| 5,493,177 A | 2/1996 | Muller |
| 5,500,569 A | 3/1996 | Blomberg |
| 5,542,016 A | 7/1996 | Kaschke |
| 5,616,986 A | 4/1997 | Jacobsen |
| 5,644,676 A | 7/1997 | Blomberg |
| 5,658,976 A | 8/1997 | Carpenter |
| 5,669,692 A | 9/1997 | Thorgersen |
| 5,671,050 A | 9/1997 | De Groot |
| 5,674,698 A | 10/1997 | Zarling |
| 5,690,417 A | 11/1997 | Polidor et al. |
| 5,715,083 A | 2/1998 | Takayama |
| 5,719,391 A | 2/1998 | Kain |
| 5,757,014 A | 5/1998 | Bruno |
| 5,781,338 A | 7/1998 | Kapitza et al. |
| 5,803,579 A | 9/1998 | Turnbull et al. |
| 5,804,919 A | 9/1998 | Jacobsen |
| 5,808,759 A | 9/1998 | Okamori et al. |
| 5,827,438 A | 10/1998 | Blomberg |
| 5,833,827 A | 11/1998 | Anazawa |
| 5,858,562 A | 1/1999 | Utsugi |
| 5,864,426 A | 1/1999 | Songer |
| 5,942,319 A | 8/1999 | Oyama |
| 5,955,839 A | 9/1999 | Jaffe |
| 5,984,861 A | 11/1999 | Crowley |
| 6,110,106 A | 8/2000 | MacKinnon et al. |
| 6,154,282 A | 11/2000 | Lilge et al. |
| 6,198,211 B1 | 3/2001 | Jaffe |
| 6,204,971 B1 | 3/2001 | Morris |
| 6,222,673 B1 | 4/2001 | Austin |
| 6,293,911 B1 | 9/2001 | Imaizumi et al. |
| 6,299,338 B1 | 10/2001 | Levinson |
| 6,304,584 B1 | 10/2001 | Krupke |
| 6,366,383 B1 | 4/2002 | Roeder |
| 6,392,341 B2 | 5/2002 | Jacobsen |
| 6,404,127 B2 | 6/2002 | Jacobsen |
| 6,404,495 B1 | 6/2002 | Melman |
| 6,422,994 B1 | 7/2002 | Kaneko et al. |
| 6,444,476 B1 | 9/2002 | Morgan |
| 6,513,962 B1 | 2/2003 | Mayshack et al. |
| 6,517,213 B1 | 2/2003 | Fujita et al. |
| 6,529,322 B1 | 3/2003 | Jones |
| 6,542,231 B1 | 4/2003 | Garrett |
| 6,544,734 B1 | 4/2003 | Briscoe |
| 6,594,075 B1 | 7/2003 | Kanao et al. |
| 6,608,332 B2 | 8/2003 | Shimizu |
| 6,614,161 B1 | 9/2003 | Jacobsen |
| 6,614,179 B1 | 9/2003 | Shimizu et al. |
| 6,637,905 B1 | 10/2003 | Ng |
| 6,642,652 B2 | 11/2003 | Collins |
| 6,649,432 B1 | 11/2003 | Eilers |
| 6,674,575 B1 | 1/2004 | Tandler et al. |
| 6,680,569 B2 | 1/2004 | Mueller-Mach et al. |
| 6,685,341 B2 | 2/2004 | Ouderkirk et al. |
| 6,690,467 B1 | 2/2004 | Reel |
| 6,717,353 B1 | 4/2004 | Mueller |
| 6,747,710 B2 | 6/2004 | Hall |
| 6,791,259 B1 | 9/2004 | Stokes et al. |
| 6,791,629 B2 | 9/2004 | Moskovich |
| 6,795,239 B2 | 9/2004 | Tandler et al. |
| 6,843,590 B2 | 1/2005 | Jones |
| 6,869,206 B2 | 3/2005 | Zimmerman et al. |
| 6,870,165 B2 | 3/2005 | Amirkhanian |
| 6,926,848 B2 | 8/2005 | Le Mercier |
| 6,958,245 B2 | 10/2005 | Seul et al. |
| 6,960,872 B2 | 11/2005 | Beeson et al. |
| 6,981,970 B2 | 1/2006 | Karni |
| 6,991,358 B2 | 1/2006 | Kokogawa |
| 6,995,355 B2 | 2/2006 | Rain, Jr. et al. |
| 7,009,211 B2 | 3/2006 | Eilers |
| 7,011,421 B2 | 3/2006 | Hulse et al. |
| 7,035,017 B2 | 4/2006 | Tadic-Galeb |
| 7,083,610 B1 | 8/2006 | Murray et al. |
| 7,141,801 B2 | 11/2006 | Goodwin |
| 7,153,015 B2 | 12/2006 | Brukilacchio |
| 7,192,161 B1 | 3/2007 | Cleaver et al. |
| 7,205,048 B2 | 4/2007 | Naasani |
| 7,208,007 B2 | 4/2007 | Nightingale et al. |
| 7,211,833 B2 | 5/2007 | Slater, Jr. et al. |
| 7,239,449 B2 | 7/2007 | Leitel et al. |
| 7,300,175 B2 | 11/2007 | Brukilacchio |
| 7,316,497 B2 | 1/2008 | Rutherford et al. |
| 7,384,797 B1 | 6/2008 | Blair |
| 7,416,313 B2 | 8/2008 | Westphal et al. |
| 7,422,356 B2 | 9/2008 | Hama et al. |
| 7,427,146 B2 | 9/2008 | Conner |
| 7,445,340 B2 | 11/2008 | Conner |

(56) References Cited

U.S. PATENT DOCUMENTS

| | | | |
|---|---|---|---|
| 7,467,885 B2 | 12/2008 | Grotsch et al. | |
| 7,488,088 B2 | 2/2009 | Brukilacchio | |
| 7,488,101 B2 | 2/2009 | Brukilacchio | |
| 7,498,734 B2 | 3/2009 | Suehiro et al. | |
| 7,540,616 B2 | 6/2009 | Conner | |
| 7,633,093 B2 | 12/2009 | Blonder et al. | |
| 7,709,811 B2 | 5/2010 | Conner | |
| 7,746,560 B2 | 6/2010 | Yamazaki | |
| 7,832,878 B2 | 11/2010 | Brukilacchio | |
| 7,837,348 B2 | 11/2010 | Narendran et al. | |
| 7,846,391 B2 | 12/2010 | Jaffe et al. | |
| 7,854,514 B2 | 12/2010 | Conner | |
| 7,857,457 B2 | 12/2010 | Rutherford et al. | |
| 7,898,665 B2 | 3/2011 | Brukilacchio et al. | |
| 8,029,142 B2 | 10/2011 | Conner | |
| 8,098,375 B2 | 1/2012 | Brukilacchio | |
| 8,242,462 B2 | 8/2012 | Jaffe et al. | |
| 8,258,487 B1 | 9/2012 | Jaffe et al. | |
| 8,263,949 B2 | 9/2012 | Jaffe et al. | |
| 8,279,442 B2 | 10/2012 | Brukilacchio et al. | |
| 8,309,940 B2 | 11/2012 | Jaffe et al. | |
| 2001/0055208 A1 | 12/2001 | Kimura | |
| 2002/0109844 A1 | 8/2002 | Christel et al. | |
| 2002/0127224 A1 | 9/2002 | Chen | |
| 2002/0136001 A1* | 9/2002 | Lefkovitz et al. | 362/147 |
| 2003/0007087 A1 | 1/2003 | Hakamata et al. | |
| 2003/0044160 A1 | 3/2003 | Jones et al. | |
| 2003/0095401 A1 | 5/2003 | Hanson et al. | |
| 2003/0127609 A1 | 7/2003 | El-Hage et al. | |
| 2003/0160151 A1 | 8/2003 | Zarate et al. | |
| 2003/0230728 A1 | 12/2003 | Dai | |
| 2003/0233138 A1 | 12/2003 | Spooner | |
| 2004/0090600 A1 | 5/2004 | Blei | |
| 2004/0247861 A1 | 12/2004 | Naasani | |
| 2004/0264185 A1 | 12/2004 | Grotsch et al. | |
| 2005/0062404 A1 | 3/2005 | Jones et al. | |
| 2005/0116635 A1 | 6/2005 | Walson et al. | |
| 2005/0146652 A1 | 7/2005 | Yokoyama et al. | |
| 2005/0152029 A1 | 7/2005 | Endo | |
| 2005/0184651 A1 | 8/2005 | Cheng | |
| 2005/0201899 A1 | 9/2005 | Weisbuch | |
| 2005/0248839 A1 | 11/2005 | Yamaguchi | |
| 2005/0260676 A1 | 11/2005 | Chandler | |
| 2005/0263679 A1 | 12/2005 | Fan | |
| 2006/0002131 A1 | 1/2006 | Schultz et al. | |
| 2006/0030026 A1 | 2/2006 | Garcia | |
| 2006/0060872 A1 | 3/2006 | Edmond et al. | |
| 2006/0060879 A1 | 3/2006 | Edmond | |
| 2006/0114960 A1 | 6/2006 | Snee | |
| 2006/0170931 A1 | 8/2006 | Guo | |
| 2006/0237658 A1 | 10/2006 | Waluszko | |
| 2006/0282137 A1 | 12/2006 | Nightingale et al. | |
| 2007/0009210 A1 | 1/2007 | Hulse | |
| 2007/0053184 A1 | 3/2007 | Brukilacchio | |
| 2007/0053200 A1 | 3/2007 | Brukilacchio | |
| 2007/0058389 A1 | 3/2007 | Brukilacchio | |
| 2007/0064202 A1 | 3/2007 | Moffat et al. | |
| 2007/0086006 A1 | 4/2007 | Ebersole et al. | |
| 2007/0126017 A1 | 6/2007 | Krames et al. | |
| 2007/0211460 A1 | 9/2007 | Ravkin | |
| 2007/0253733 A1 | 11/2007 | Fey | |
| 2007/0279914 A1 | 12/2007 | Rutherford et al. | |
| 2007/0279915 A1 | 12/2007 | Rutherford et al. | |
| 2007/0280622 A1 | 12/2007 | Rutherford et al. | |
| 2007/0281322 A1 | 12/2007 | Jaffe et al. | |
| 2007/0284513 A1 | 12/2007 | Fan | |
| 2007/0297049 A1 | 12/2007 | Schadwinkel et al. | |
| 2008/0079910 A1 | 4/2008 | Rutherford et al. | |
| 2008/0224024 A1 | 9/2008 | Ashdown | |
| 2008/0291446 A1 | 11/2008 | Smith | |
| 2009/0086479 A1* | 4/2009 | Suehiro et al. | 362/234 |
| 2009/0122533 A1 | 5/2009 | Brukilacchio | |
| 2009/0196046 A1 | 8/2009 | Rutherford et al. | |
| 2009/0268461 A1 | 10/2009 | Deak et al. | |
| 2010/0188017 A1 | 7/2010 | Brukilacchio | |
| 2011/0044858 A1 | 2/2011 | Jaffe et al. | |
| 2012/0106192 A1 | 5/2012 | Brukilacchio | |
| 2012/0181936 A1 | 7/2012 | Jaffe et al. | |
| 2012/0181937 A1 | 7/2012 | Jaffe et al. | |
| 2012/0238472 A1 | 9/2012 | Jaffe et al. | |
| 2012/0252704 A1 | 10/2012 | Jaffe et al. | |

FOREIGN PATENT DOCUMENTS

| | | |
|---|---|---|
| GB | 0943756 | 12/1963 |
| GB | 2 000 173 A | 1/1979 |
| JP | 02-804873 | 7/1998 |
| JP | 2005-195485 | 7/2005 |
| JP | 2005-243973 | 9/2005 |
| JP | 2006-049814 | 2/2006 |
| JP | 2007-133435 | 5/2007 |
| KR | 10-2006-0055934 | 5/2006 |
| KR | 10-2006-0089104 | 8/2006 |
| WO | WO 02/080577 | 10/2002 |
| WO | WO 2004/114053 | 12/2004 |
| WO | WO 2006/067885 | 6/2006 |
| WO | WO 2006/120586 | 11/2006 |

OTHER PUBLICATIONS

International Search Report dated Dec. 31, 2008, Application No. PCT/US2008/072394, 10 pages.

International Search Report for PCT/US2010021843 dated Aug. 19, 2010, 9 pages.

Extended European Search Report for PCT/US2008072394 dated Oct. 7, 2011, 9 pages.

International Search Report dated Jun. 19, 2012 for Application No. PCT/US2011/063030, 11 pages.

Extended European Search Report for PCT/US2007/069490 dated Oct. 26, 2012, 8 pages.

Albrecht, M., et al., "Scintillators and Wavelength Shifters for the Detection of Ionizing Radiation," Astroparticle, Particle and Space Physics, Detectors and Medical Physics Applications, ICATPP-8, M. Barone, et al., Eds, World Scientific, pp. 502-511 (2004).

Da-Lite Screen Company, Inc., www.da-lite.com, 46 pages website downloads as of Oct. 8, 1998.

DDS™ Rear Projection Screens, LORS™ Reflection Screens, © 1998 Physical Optics Corporation, Torrance, CA, 2 pages.

Deck, L., et al., "Two color light-emitting-diode source for high precision phase-shifting interferometry", Optics Letters, vol. 18, No. 22, Nov. 15, 1993, pp. 1899-1901.

Depp, S.W., et al., "Flat Panel Displays," Scientific American, pp. 90-97, Mar. 1993.

Flor-Henry, M., et al., "Use of a Highly Sensitive Two-Dimensional Luminescence Imaging System to Monitor Endogenous Bioluminescence in Plant Leaves," BMC Plant Biology, vol. 4, No. 19, Nov. 2004.

Hamberg, I. and Granqvist, C.G., "Evaporated Sn-doped $In_2O_3$ films: Basic optical properties and applications to energy-efficient windows," Journal of Applied Physics, vol. 60, No. 11, pp. R123-R159, Dec. 1, 1986.

Handbook of Optics, vol. 1—Fundamentals, Techniques, and Design, Second Edition, Chapter 42: Optical Properties of Films and Coatings, J.A. Dobrowolski, pp. 42.3-42.25, McGraw-Hill, Inc., © 1995.

Haroche, S., et al., "Cavity Quantum Electrodynamics," Scientific American, pp. 54-62, Apr. 1993.

Hecht, Jeff, "Diverse fiberoptic systems require varied sources," Laser Focus World, vol. 36, No. 1, pp. 155-161, Jan. 2000.

Hemingway, D.J. and Lissberger, P.H., "Effective Refractive Indices of Metal-Dielectric Interference Filters," Applied Optics, vol. 6, No. 3, pp. 471-476, Mar. 1967.

Holloway, R.J. and Lissberger, P.H., "The Design and Preparation of Induced Transmission Filters," Applied Optics, vol. 8, No. 3, pp. 653-660, Mar. 1969.

Huo, D.T.C., et al., "Reticulated Single-Crystal Luminescent Screen," J. Electrochem. Soc., vol. 133, No. 7, pp. 1492-1497, Jul. 1986.

(56) References Cited

OTHER PUBLICATIONS

Jenmar Visual Systems, Sunnyvale, CA, 4 pages, no date, but at least as early as Oct. 15, 1998.

Landau, B.V. and Lissberger, P.H., "Theory of Induced-Transmission Filters in Terms of the Concept of Equivalent Layers," Journal of the Optical Society of America, vol. 62, No. 11, pp. 1258-1264, Nov. 1972.

Launer, Herbert F., "Exposure Meter for Precision Light Dosage", The Review of Scientific Instruments, vol. 20, No. 2, Feb. 1949, pp. 103-109.

Lissberger, P.H., "Coatings with Induced Transmission," Applied Optics, vol. 20, No. 1, pp. 95-103, Jan. 1, 1981.

Mauch, R.H., et al., "Optical Behaviour of Electroluminescent Devices," Springer Proceedings in Physics, vol. 38, Electroluminescence, © Springer-Verlag Berlin, Heidelberg, pp. 291-295 (1989).

Morgan, C. G., et al., "New Approaches to Lifetime-Resolved Luminescence Imaging", Journal of Fluorescence, vol. 7, No. 1, 1997, pp. 65-73.

Pelletier, E. and Macleod, H.A., "Interference Filters with Multiple Peaks," Journal of the Optical Society of America, vol. 72, No. 6, pp. 683-687, Jun. 1982.

Plasma Display Manufacturers of the American Display Consortium, "Recommended Research Topics on Plasma Display for the DARPA Sponsored Phosphor Center of Excellence," pp. 1-2, Mar. 24, 1993.

Poelman, D., et al., "Spectral Shifts in Thin Film Electroluminescent Devices: An Interference Effect," J. Phys. D: Appl. Phys., vol. 25, pp. 1010-1013 (1992).

Schott Glass Technologies, Inc., Schott Total Customer Care, Contrast Enhancement Filters, Duryea, PA, 6 pages, Jan. 1998.

Schubert, E.F., et al., "Giant Enhancement of Luminescence Intensity in Er-doped $Si/SiO_2$ Resonant Cavities," Appl. Phys. Lett. vol. 61, No. 12, pp. 1381-1383, Sep. 21, 1992.

Stewart Filmscreen Corporation®, www.stewartfilm.com, 34 pages website downloads as of Oct. 8, 1998.

Tuenge, R.T., "Current Status of Color TFEL Phosphors," Electroluminescence—Proceedings of the Sixth International Workshop on Electroluminescence, El Paso, Tex., pp. 173-177, May 1992.

Vlasenko, N.A., et al., "Interference of Luminescent Emission from an Evaporated Phosphor," Opt. Spect., vol. 11, pp. 216-219 (1961).

Vlasenko, N.A., et al., "Investigation of Interference Effects in Thin Electroluminescent ZnS—Mn Films," Opt. Spect., vol. 28, pp. 68-71 (1970).

Whitaker, Jerry C., "Electronic Displays: Technology, Design, and Applications," McGraw-Hill, Inc., pp. 185-192 (1994).

World Watch, Photonics Spectra, "IR Reflective Coating Boosts Bulb's Output, Recycling of IR Energy Saves Power, Cuts Costs" pp. 40-41, Jan. 1991.

Yamamoto, Y., et al., "Optical Processes in Microcavities," Physics Today, pp. 66-73, Jun. 1993.

Yokoyama, H., "Physics and Device Applications of Optical Microcavities," Science, vol. 256, pp. 66-70, Apr. 3, 1992.

Young, L., "Multilayer Interference Filters with Narrow Stop Bands," Applied Optics, vol. 6, No. 2, pp. 297-312, Feb. 1967.

\* cited by examiner

FIG. 1
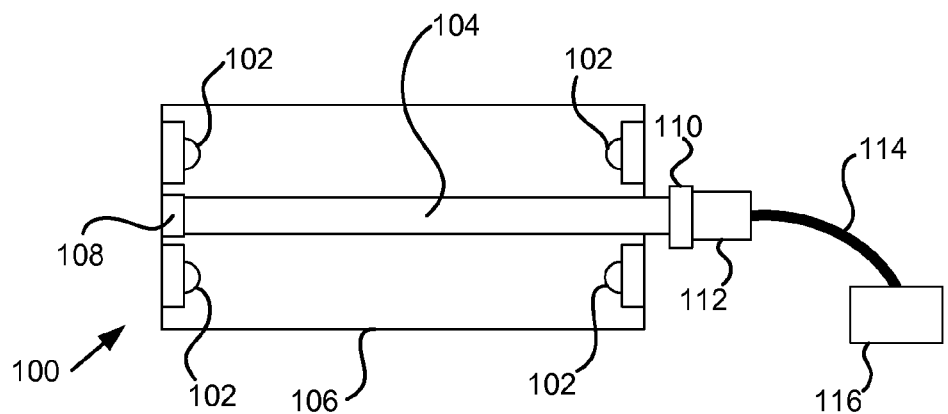
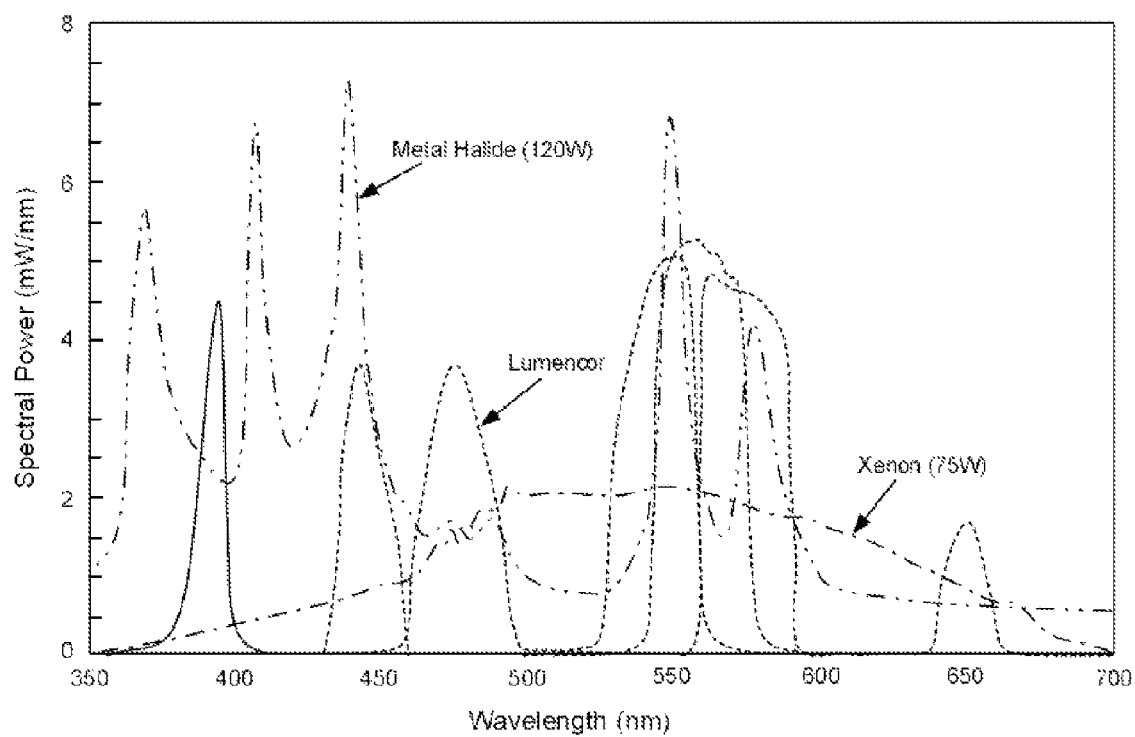
FIG. 2

FIG. 3
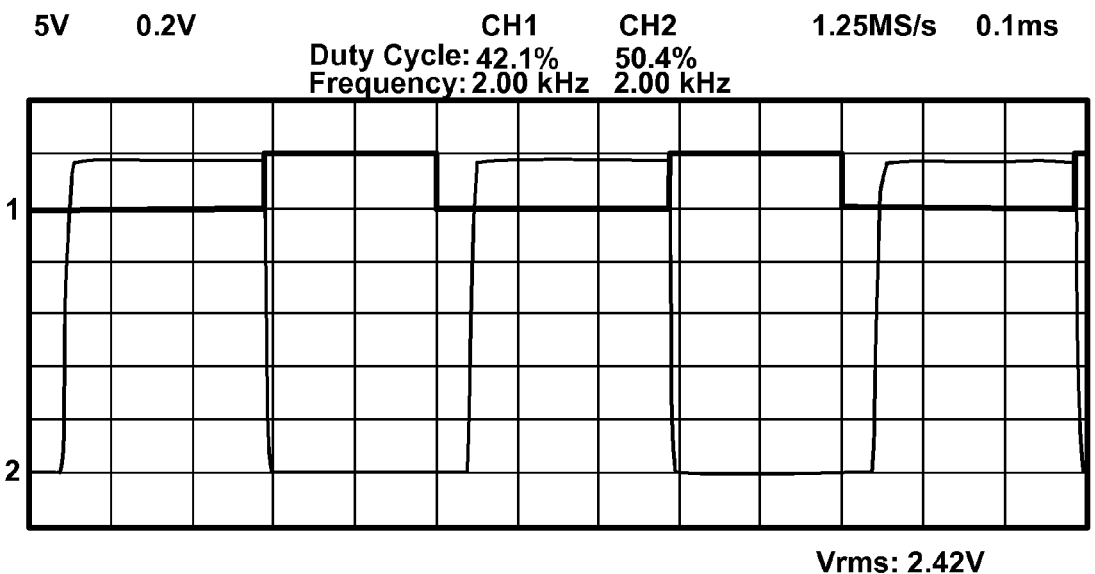
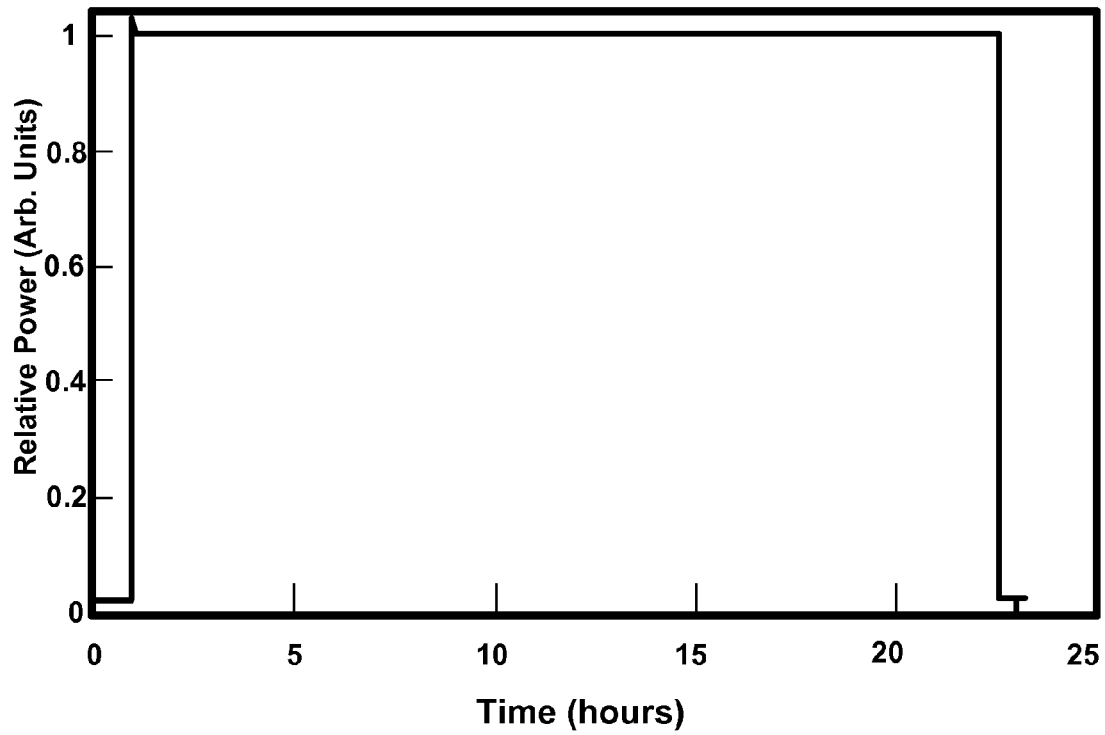
FIG. 4

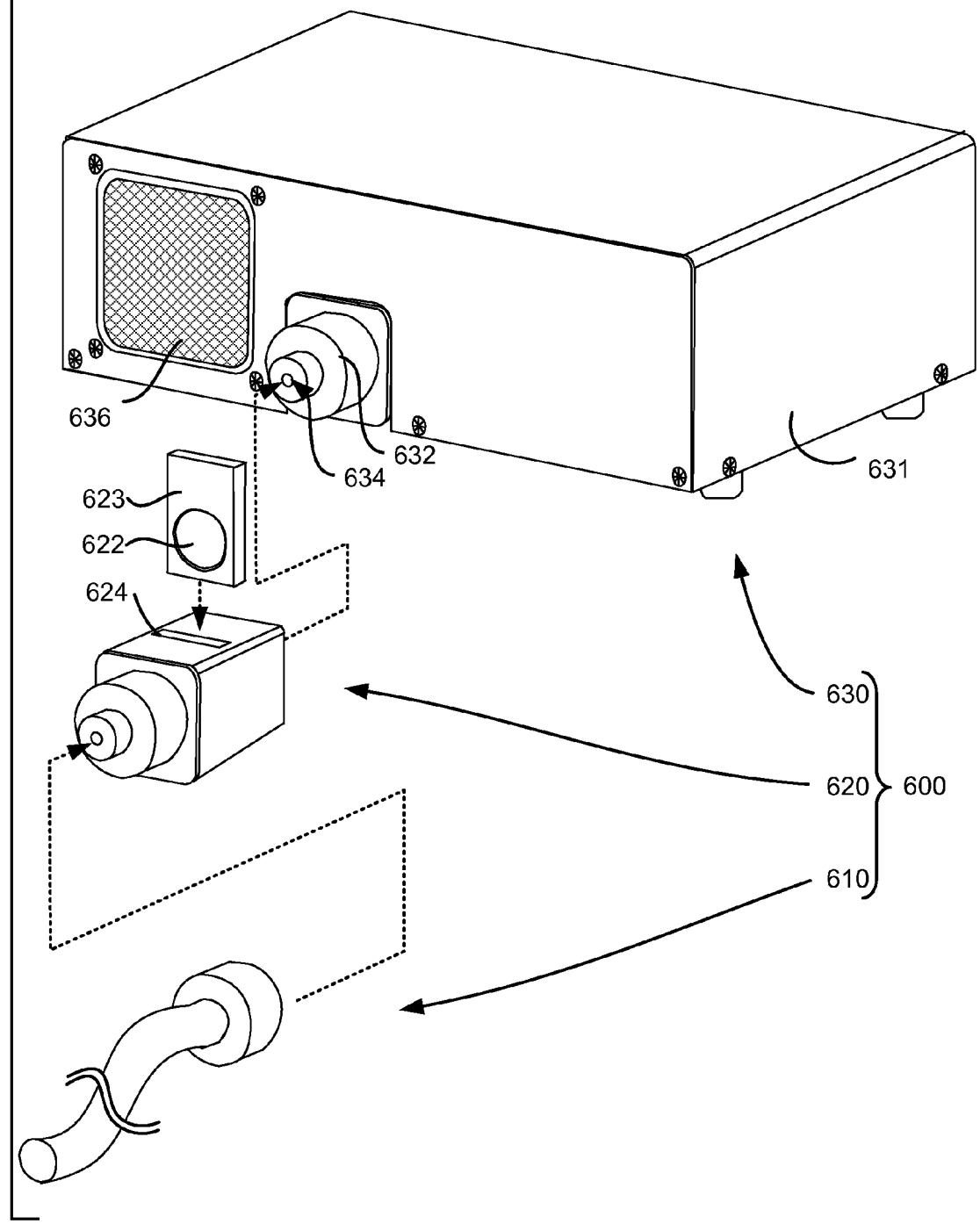

FIG. 10A
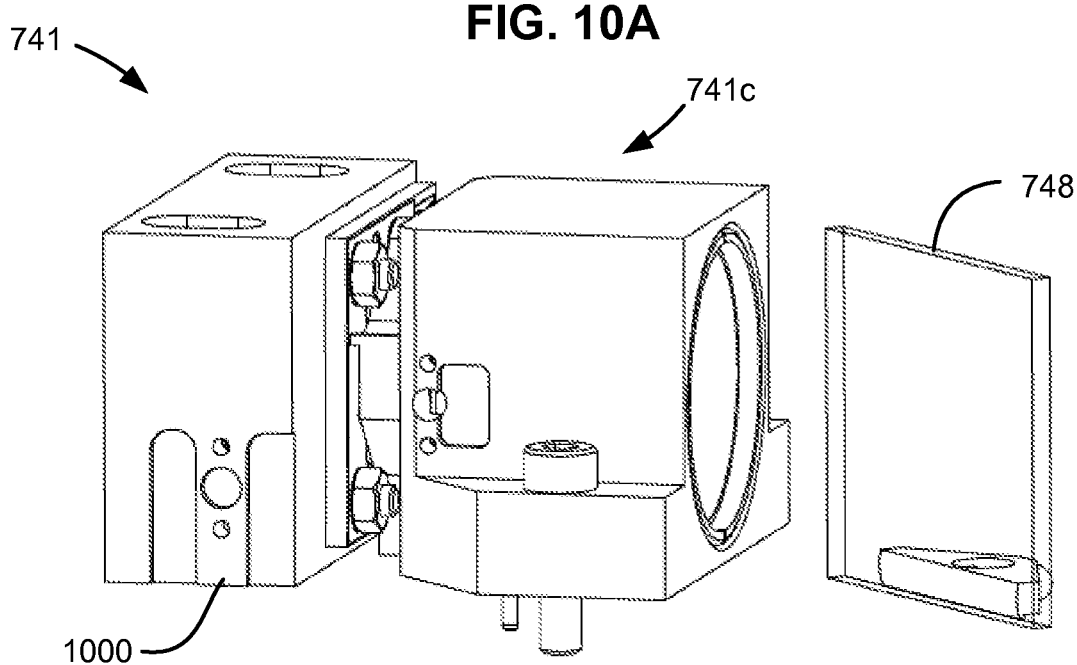
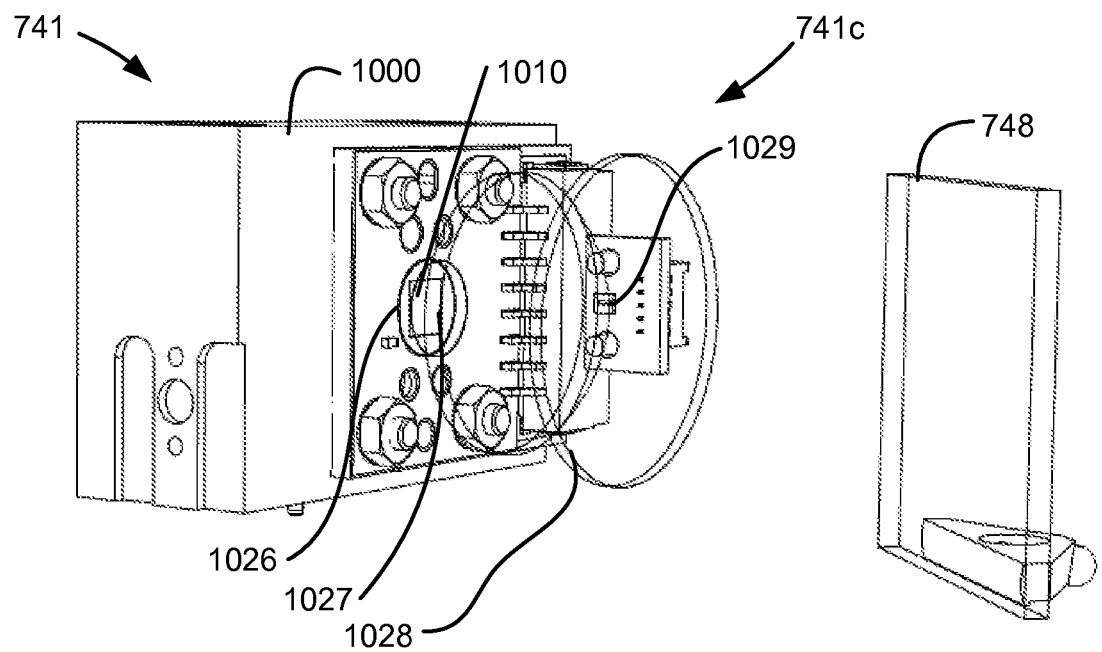
FIG. 10B

FIG. 11A
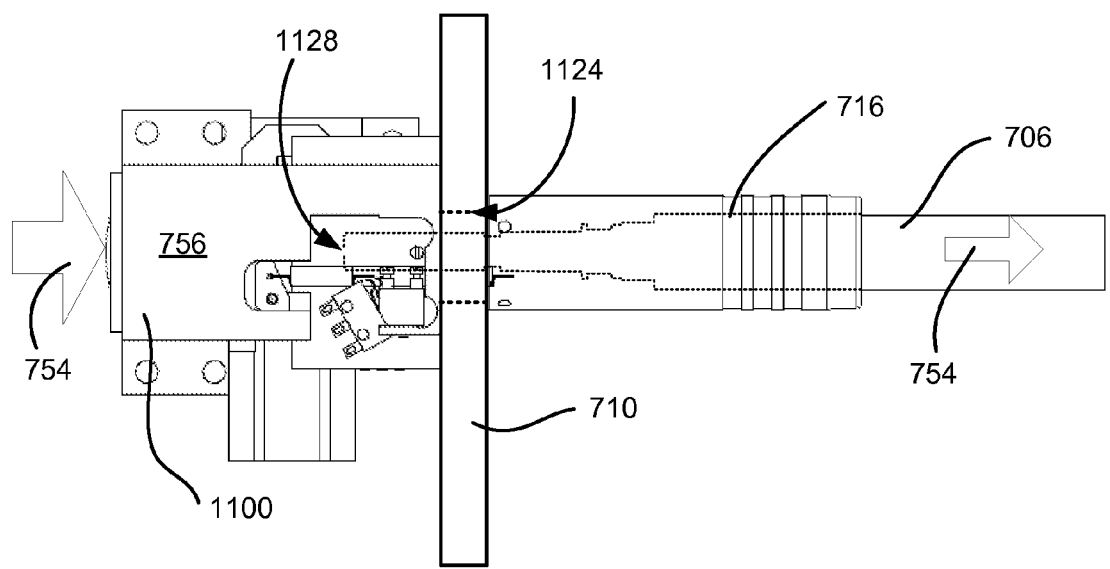
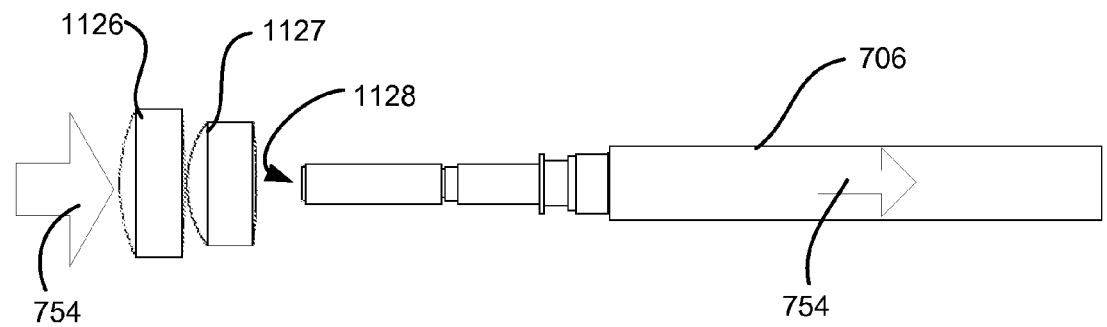
FIG. 11B

SOLID STATE CONTINUOUS WHITE LIGHT SOURCE

CLAIM OF PRIORITY

The present application claims priority to U.S. Provisional Patent Application No. 61/589,086, filed Jan. 20, 2012, entitled "SOLID STATE CONTINUOUS WHITE LIGHT SOURCE"; and U.S. Provisional Patent Application No. 61/644,921, entitled "SOLID STATE CONTINUOUS WHITE LIGHT SOURCE", filed May 9, 2012, which applications are incorporated herein by reference in their entireties.

RELATED APPLICATIONS

The present application is related to the following patents and patent applications which are incorporated herein by reference in their entireties:

U.S. Pat. No. 8,242,462, granted Jan. 1, 2010, entitled "Lighting Design of High Quality Biomedical Devices"; and U.S. Pat. No. 7,846,391, granted Dec. 7, 2010, entitled "Bioanalytical Instrumentation Using A Light Source Subsystem," U.S. Publication No. 2007/0281322 filed May 21, 2007; and U.S. Pat. No. 7,709,811, granted May 4, 2010 entitled "Light Emitting Diode Illumination System," U.S. Publication No. 2009/0008573 filed Jul. 2, 2008; and U.S. Pat. No. 8,098,375, granted Jan. 17, 2012 entitled "Light Emitting Diode Illumination System," U.S. Publication No. 2009/0040523 filed Aug. 5, 2008; and U.S. patent application Ser. No. 13/012,658, filed Jan. 24, 2011 entitled "Light Emitting Diode Illumination System," U.S. Publication No. 2011/0116261.

FIELD OF THE INVENTION

The present invention relates to lighting systems for life sciences applications including microscopy, endoscopy, and diagnostics and analytical applications. In particular the present invention relates to solid state light sources for microscopy, endoscopy, and fluorescence imaging.

BACKGROUND OF THE INVENTION

Light is a powerful tool in many of today's most widely used life science instruments, including microscopes, endoscopes, analytical instruments, diagnostic instruments, medical devices and miniaturized analyzers. Reliable high intensity, low cost light engines are essential to the design and proliferation of these life science instruments.

Lighting for life sciences is a broad and general category. The specifications for the power and spectral content of the light are varied and so too are the equally important optical delivery requirements. Spectral and spatial lighting requirements for sensing on the head of an optical probe or within a single cell in a flowing stream differ in output power by orders of magnitude from the requirements of a multi-analyte detection scheme on an analysis chip or within the wells of a micro-titer plate. The number of colors, spectral purity, spectral and power stability, durability and switching requirements are each unique. Illuminating hundreds of thousands of spots for quantitative fluorescence within a micro-array may be best served by projection optics while microscopes set demanding specifications for light delivery to overfill the back aperture of the microscope objective within optical trains specific to each scope body and objective design.

Arc lamps are noted to be flexible sources in that they provide white light. The output is managed, with numerous optical elements, to select for the wavelengths of interest and, for typical fluorescence based instruments, to discriminate against the emission bands. However arc lamps are notorious for instability, lack of durability, large power demands, large size, and significant heat management requirements, which make them less than ideal for life science instruments and particularly portable instruments.

Lasers can provide high power coherent light in particular colors dependent upon their design. Lasers require a trained user and significant safety precautions. While solid state red outputs are cost effective, the shorter wavelength outputs are typically costly, require significant maintenance and ancillary components. Color balance and drift for multi-line outputs is a serious complication to quantitative analyses based on lasers. Moreover, the bulk of fluorescence applications do not need coherent light, are complicated by speckle patterns and do not require such narrow band outputs. Overcoming each of these traits requires light management and adds cost to the implementation of lasers for use in life science instruments.

LEDs (light-emitting diodes) have matured significantly within the last decades. LEDs are now available in a relatively wide range of wavelengths. Their output is broad, but, output in the visible spectrum is profoundly reduced in the green wavelengths, 500-600 nm (the so called "green gap"). LEDs presents trade-offs with respect to emission wavelength dependent intensity, broad emission spectrum (spectral half width on the order of 30 nm or more), poor spectral stability, and the wide angular range of emission. In addition, the process used to manufacture LED's cannot tightly control their spectral stability; anyone wishing to use LED's in applications requiring a good spectral stability typically works directly with a supplier to essentially hand-pick the LED's for the particular application. Moreover the spectral output of an LED varies with temperature. Also, LED's emit light over a wide angular range (50% of light intensity emitted at 70°). While optics can narrow the emission band and focus the light output, the resulting loss in power and increase in thermal output further complicates the use of LEDs in light engines.

Most importantly, the fundamental light source technologies (e.g. lasers and LEDs) cannot be readily improved for bioanalytical applications. The light engine market simply does not justify the large investment necessary to overcome fundamental performance limitations in the lasers and LEDs themselves. Moreover the numerous manufacturers of lamps and lasers provide only a source, not an integrated light engine. Companies such as ILC Technology, Lumileds, Spectra-Physics, Sylvania and CoolLED, Ltd. produce light engines which require some sort of mechanics and or electro-optics such as acousto-optic tunable filters (AOTFs), excitation filters (with a wheel or cube holder), shutters and controllers. As a result, the performance and price of life science instruments instrument is constrained by the available light source technologies and light engines which utilize them. Accordingly there is a need for solid state light engines which overcome the limitations of the present technology.

SUMMARY OF THE INVENTION

The present invention provides a solid state light engine for life science applications including variations suitable for use in microscopes, endoscopes, analytical instruments, diagnostic instruments, medical devices and miniaturized analyzers. The solid state light engine is an inexpensive lighting solution, uniquely well suited to the production of safe, effective and commercially viable life science instruments and biomedical devices. In an embodiment of the invention, this light engine can provide powerful, pure, stable, inexpensive light across the visible spectrum. Light engines are designed to directly replace the entire configuration of light management components with a single, simple unit. Power, spectral breadth and purity, stability and reliability data demonstrates the advantages of these light engines for today's life science instrument needs. Performance and cost analyses are superior to traditional optical subsystems based on lamps, lasers and LEDs with respect to their suitability as sources for life sciences applications, implementation for development/evaluation of novel measurement tools and overall superior reliability. Using solid state light engines of the present invention, the demand for portable, hand-held analyzers and disposable devices with highly integrated light sources can be fulfilled.

Embodiments of the present invention are directed to a solid state white-light engine suitable for use as a replacement for conventional arc light, Metal Halide and Xenon white-light subsystems for applications in life sciences including, for example, microscopy, fluorescence microscopy, and endoscopy. In particular embodiments, the solid state light engine generates white light which is continuous in the visible spectrum from 380 nm to 650 nm. In particular embodiments the solid state white-light engine incorporates one or more light pipe engines.

In some embodiments of the present invention, the light engine emits high quality white light having a color rendering index greater than 85. In an embodiment of the present invention, the output of light engine can be pulsed on and off as desired at high frequency. In an embodiment of the present invention, the output of light engine can be pulsed on and off in synchronization with light collection to allow time-based fluorescence detection.

In a particular embodiment the present invention is directed to a to a solid state white-light engine which emits white light having a spectral power equal to or greater than the spectral power of a 120 W metal halide lamp or 150 W Xenon lamp across substantially the entire visible spectrum from 380 nm to 650 nm. In particular embodiments the spectral power is greater than 1 mW/nm over the substantially the entire visible spectrum from 380 nm to 650 nm and greater than 3 mW/nm over the range from 500-600 nm.

In a particular embodiment the present invention is directed to a solid state light engine which has a plurality of LED light sources and is capable of emitting light having a spectral power equal to or greater than the spectral power of a 120 W metal halide lamp or 150 W Xenon lamp across substantially the entire visible spectrum from 380 nm to 650 nm. The LED light sources can be selectable controlled in order to select the spectral power distribution of the light output.

Another embodiment of the present invention relates to an improved system for cooling the light sources of a light engine which reduces contamination of the light sources and optical pathway from cooling airflow. The system includes means for transmission of heat away from LED light sources and light pipe engines to a remote heat sink.

Other objects and advantages of the present invention will become apparent to those skilled in the art from the following description of the various embodiments, when read in light of the accompanying drawings.

BRIEF DESCRIPTION OF THE FIGURES

Various embodiments of the present invention can be described in detail based on the following figures.

FIG. 1 shows a schematic of a light engine subsystem consisting of a lamp module and delivery optics.

FIG. 2 shows light engine output relative to a typical metal halide lamp and 75 W xenon bulb.

FIG. 3 shows light pipe engine with <10 ns rise and fall times for fast switching between bands.

FIG. 4 shows light engine stability over 24 hours of use.

FIG. 6A shows a white light illumination system according to an embodiment of the present invention.

FIG. 10A shows a perspective view of an LED light source subsystem of the solid state illumination system of FIGS. 7A to 7E according to an embodiment of the present invention.

FIG. 10B shows a partial perspective view of the LED light source subsystem of FIG. 10A.

FIG. 11A shows a top view of an output optics subsystem of the solid state illumination system of FIGS. 7A to 7E according to an embodiment of the present invention.

FIG. 11B shows a top view of the optical components of the output optics subsystem of FIG. 11A.

Figure 5:
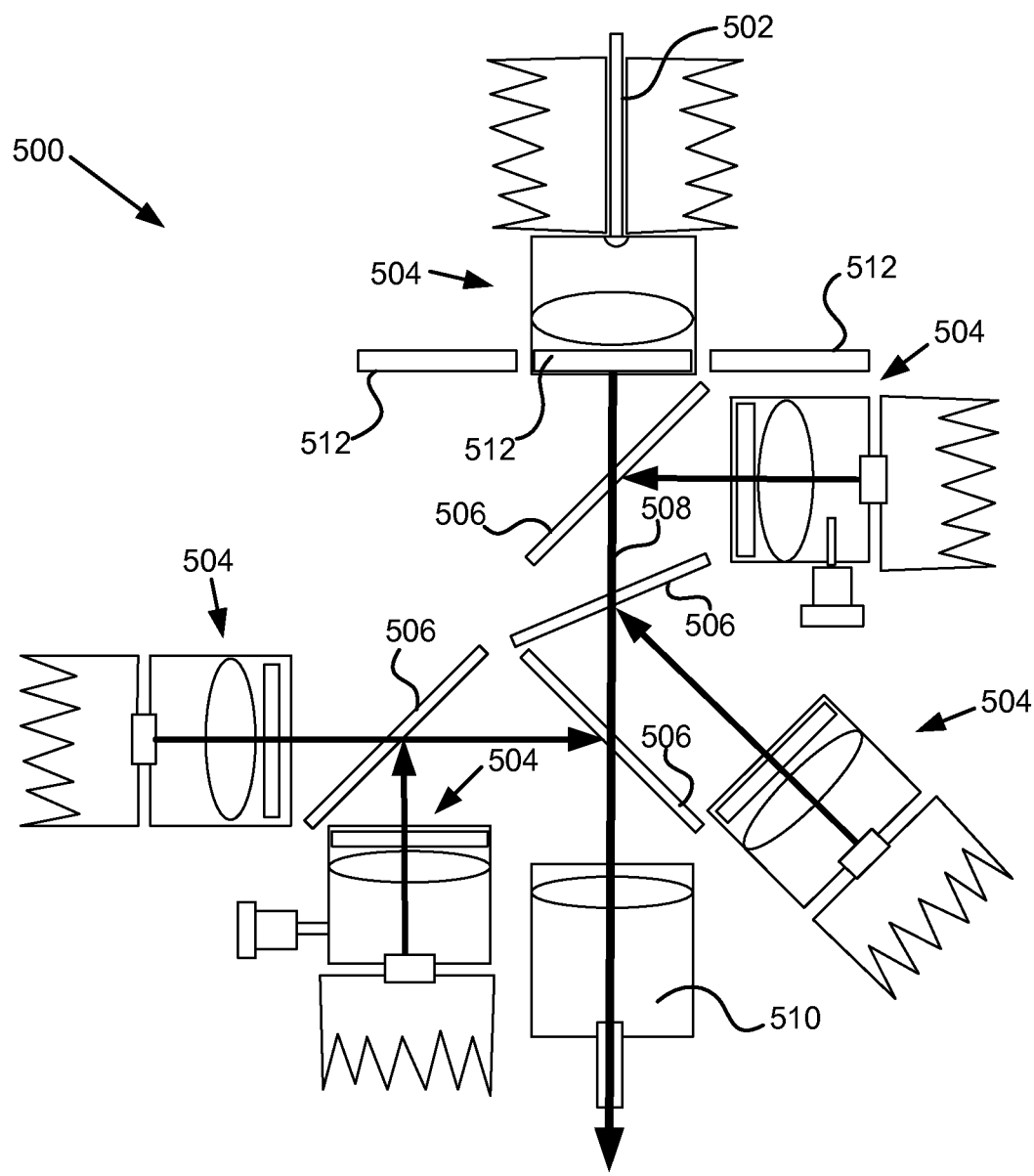
FIG. 5 shows an eight color light engine layout, including a light pipe and five other solid state light sources, with dichroic mirrors to create a single coaxial 8-color beam.

In the figures common reference numerals are used to indicate like elements throughout the drawings and detailed description; therefore, reference numerals used in a drawing may or may not be referenced in the detailed description specific to such drawing if the associated element is described elsewhere. The first digit in a three digit reference numeral indicates the series of figures in which the referenced item first appears. Likewise the first two digits in a four digit reference numeral.

DETAILED DESCRIPTION OF THE INVENTION

While lighting manufacturers cannot provide all things to all applications, it is precisely this breadth of demand for which a light engine can be designed. To that end, products are not simple sources, but rather light engines: sources and all the ancillary components required to provide pure, powerful, light to the sample or as close to it as mechanically possible. Such designs have resulted in products that embody a flexible, hybrid solution to meet the needs of the broad array of applications for biotech. A qualitative comparison of light engine performance as a function of source technology is summarized in Table 1.

TABLE I

A qualitative comparison of light engine performance as function of the source technology employed.

| Source Technology | Useable Light | Uniformity | Temporal Response | Heat Generation | Durability | Cost |
|---|---|---|---|---|---|---|
| Arc Lamp | med | poor | none | high | low | high |
| Laser | high | poor | none | low | low | very high |
| LED | low | poor | fast | low | high | medium |
| Tungsten | low | poor | none | medium | low | medium |
| Light Pipe | high | high | fast | low | high | low |

Light Pipe Engines

While no one lighting solution can best satisfy all instrument architectures, a light pipe engine combines the best of solid state technologies to meet or outperform the traditional technologies listed in Table I on the basis of all figures of merit for all individual wavelengths. Key to this performance is the light pipe architecture. Single outputs, such as red from a diode laser, may be competitive. However, no family of outputs can by assembled that bests the light pipe engines disclosed herein. In an embodiment of the invention, a light pipe engine can emit narrowband light exceeding 500 mW/color with intensifies up to 10 W/cm² depending on the application. In an embodiment of the invention, bandwidths as narrow as 10 nm are achievable. While such output power and overall emission intensity is impressive, the most significant figure of merit for quantifying the value of any lighting subsystem for bio-analytics is the intensity of high quality illumination provided to the sample. This is a factor dictated by the instrument design and sample volume and clearly very application specific.

In the case of medical devices and portable diagnostics the present light pipe invention offers a smart alternative for light generation. The light pipe engine is an optical subsystem; it consists of lamp modules for each discrete output based on solid state technologies tailored to best satisfy that output requirement complete with collection and delivery optics. The capabilities of the light pipe engine are highlighted in Table 2. The high performance illumination provided by the light pipe engine is embodied in a single compact unit designed to replace the entire ensemble of lighting components. The sources, excitation filters, multicolor switching capabilities and fast pulsing are contained within one box such that no external optics or mechanics are required.

TABLE II

Light pipe engine metrics of light pipe engines designed to meet the needs for portable fluorescence assays and biomedical devices.

Key Metrics:

| | |
|---|---|
| Spectral Output | Up to eight colors spanning UV-Vis-NIR<br>>_100 mW/spectral band<br>1-10 W/cm |
| Peak Wavelength | Optimal for different floors, adjustable bandwidths |
| Power Stability | >99% over 24 hours |
| Spectral Width | 10 to 50 nm |
| Spectral Drift | <1% in 24 hours |
| Color Dependence | None |
| Lifetime | >5000 hrs |
| Footprint | amenable to portability |
| Maintenance | None, no consumable components for the light engine's lifetime |

In various embodiments of the present invention, a lamp emits wavelengths of light, which excite fluorescence from photosensitive targets in the sample of interest. In various embodiments of the present invention, a lamp can be in the form of a tube, rod, or fiber of varying or constant diameter. In various embodiments of the present invention, a constituent light pipe can be made of glass, plastic, single or multiple inorganic crystal(s), or a confined liquid. In various embodiments of the present invention, a pipe either contains or is coated with a layer or layers containing, a narrow band luminescent material such as organic or inorganic compounds involving rare earths, transition metals or donor-acceptor pairs. In various embodiments of the present invention, a lamp emits confined luminescence when excited by IR, UV, or visible light from an LED, Laser, fluorescent tube, arc lamp, incandescent lamp or other light source. In an embodiment of the present invention, a lamp operates through the process of spontaneous emission, which results in a much larger selection of available wavelengths than is available for efficient stimulated emission (laser action). A number of lamps each emitting one or more color of light can have their constituent light pipes coupled in parallel or in series acting to produce multiple colors simultaneously or in sequence. Lamps can be illuminated continuously or can be pulsed on and off rapidly to enable time-based detection methods. A lamp can be switched off between measurements, to eliminate the heat output. This can be contrasted with alternatives such as arc lamps or lasers that are unstable unless they are operated continuously.

Shown in FIG. 1, is the light pipe engine 100 of an embodiment of the invention. An individual lamp module driven by light pipe technology consists of an excitation source 102, typically one or more LEDs, and a light pipe 104. In an embodiment, the excitation source 102 and light pipe 104 can be housed in a cylindrical waveguide 106. The excitation source 102 drives luminescence in the light pipe 104, which is composed of a glass or polymer fiber. In an embodiment, light pipe 104 includes a mirror 108. Glass fibers are either doped with a rare earth metal or activated with a transition metal. Polymer fibers are doped with a dye. The fibers have fast response and decay times and can achieve a high efficiency through the design of delivery optics. The design and selection of the fiber determines the peak wavelength of the output illumination; options exist to span the UV-Vis-NIR spectrum. The bandwidth of the luminescence is narrow and can be further defined with the use of band pass filters 110 integrated into the delivery optics. In an embodiment, the delivery optics may include a band pass filter 110 connected to a coupler 112, which can be attached to an optical delivery pipe 114 which leads to an instrument (e.g., a microtiter plate) 116. Output intensity is determined through the design of the pipe's excitation source.

The light pipe geometry provides a unique opportunity to shape and direct the angular and spatial range of outputs. Combined with a high output power, the delivery optics can be readily tailored to couple the light with various instruments and analyzers. Sensors, optical probes, microscope objectives or through liquid light guides, two-dimensional oligomer and micro fluidic chips, and micro titer plates are all illumination fields that light pipe engines can readily support. Moreover, high output power enables illumination of large areas within a chip, micro array or micro titer plate and, as a result, support high-speed throughput in instruments where to date only scanning modes of operation could be envisioned.

The preferred mode of light pipe excitation is the application of one or more LED's. This approach takes advantages of the benefits of LED illumination: low cost, durability, and, at an appropriate excitation wavelength, high output power to drive the light pipe. In so doing the LED's shortcomings are managed. The lack of spectral stability and the high angular output characteristic of LED's do not impact the luminescence of the light pipe. Instead, the innovation of the light pipe enables circumvention of the principle of etendue conservation. All light sources must conform to this dictate, which requires the spread of light from a source never exceed the product of the area and the solid angle. Etendue cannot decrease in any given optical system.

The ability to modulate solid-state source outputs provides a unique opportunity for multiplexed fluorescent assays. Current light engine designs employ solid state materials with fast luminescence (approximately 10 ns.) The light pipe and LED have similar modulation capabilities thus multiple light pipes tuned to different output wavelengths can be employed to selectively detect multiple fluorescent tags within a given analysis. In addition, pulse modulation and phase modulation techniques enable fluorescence lifetime detection and afford improved signal to noise ratios. Each of the solid state units is truly off when it is off so low background signals and high contrast ratios are possible.

Table III shows an embodiment of the present light pipe engine invention's product and performance features. As improvements are made to LED's and the cost of semiconductor lasers continue to decline, the tool chest of options available to light lipe engines will continue to evolve. The desired light engine can ultimately be powered by a combination of light pipe, LED's and lasers. The knowledge and competency to integrate any of these lighting technologies into the delivery optics supports the requirements of each specific application and provides technical and commercial value.

TABLE III

The light pipe engine feature set.

| | |
|---|---|
| Wavelengths | UV - Vis - NIR |
| Colors | Up to eight |
| Intensity | 1-10 W/cm$^2$ |
| Bandwidths | Adjustable |
| Size | Compact |
| Ease of Use | Yes |
| Modulation | Up to 5 kHz |
| Color control | Independent |
| System Control | Manual or computer |
| Heat output | Minimal |
| Life time | Long |

Spectral Bands and Output Power

In various embodiments of the present invention, the light pipe engine performs well compared with the output power across the visible spectrum to other lamps (see FIG. 2). Such comparisons beg for disclaimers as the outputs of the commonly employed lamps change in time and degrade with usage. The light pipe engine is all solid state so they it is significantly more stable and reproducible. FIG. 2 was taken within the manufacturers' specified lifetime for each lamp, by an independent user well trained in biophotonics, these outputs represent typical performances of a common metal halide bulb, 75 W xenon bulb and that of the light pipe engine.

Such output comparisons are further complicated by mismatches between the spikes of the metal halide bulb and light pipe light engine output bands, However, noting such disparities it is fair to claim the outputs of the light engine across the visible spectrum compare well against the outputs of a metal halide bulb in spectral windows that match the excitation energies of some of the most commonly used fluors for biotech: around 390 nm where DAPI and Hoescht can be excited; in the window most commonly associated with a cyan line of an argon ion laser and often used to excite Alexa dyes, green fluorescent proteins and fluoresceins; and in the red where neither of the lamps provides appreciable power for the likes of Cy5. The light engine also bests the Xenon lamp across the palate of excitation wavelengths most common to biotech: the Xenon lamp underperforms particularly in the violet, cyan, blue and red regions of the visible spectrum. Of course, more powerful Xenon lamps are often employed to provide enhanced performance at a significant maintenance cost.

In another embodiment of the present invention, as seen in FIG. 2, the output of the green and amber bands have essentially doubled, such that on a photon per photon basis the area under the curve for the arc lamp vs. light engine are the same. Certainly the peak shapes, and figures of merit (height, FWHM, etc.) differ. However, no compromise in output power, even for the 546 nm band of the arc lamp, should be incurred as a consequence of using a light pipe engine replacement.

Alternatively, a light pipe engine can be employed in a short duty cycle mode for power starved applications. When feasible, pulse widths of less than 100 ms at 10% duty cycles can actually improve the power output per band by a factor of 1.5 to 2.0 over longer duty cycles or in continuous mode of operation. Applications that employ multiple lasers and acousto-optic tunable filters (AOTFs) but need safe, cost effective and easy to employ lighting solutions might benefit from such light engine performance. Fluorescence microscopy for multicolor detection could take advantage of this option, for example. As could numerous other bioanalytical platforms such as a light engine replacement for the optical excitation from AOTF-based multicolor fluorescence detection for short tandem repeat (STR) analysis in a micro-eletrophoretic device, a glass microchip.

Fast Switching

Because of the solid state nature and independently operable designs of the lamp modules, coupled to fast (approximately 10 ns) decay times of typical materials employed, a light pipe based light engine outperforms any broad spectrum source in terms of support for fast analyses. Lamp based sources are coupled to filters and/or shutters with mechanical supports that relegate them 1 to 50 millisecond regimes. Even LED based lamps require filtering for most quantitative fluorescence based analyses. The light pipe based light engine incorporates all that filtering into its highly integrated design. Therefore switching times are limited today by the electronics of the boards controlling the sources. Rise times of less than 20 μs and fall times of less than 2 μs are typical (see FIG. 3). Moreover each color can be switched independently and is compatible with triggering by TTL, RS232 and USB and intensity control by RS232, USB or manually. This supports experiments where simultaneous excitation of multiple tags could previously only be done with multipass excitation filters and broadband sources. Using a light pipe engine, effectively instantaneous excitation of individual reporters can be manipulated within microsecond time frames to achieve rapid, serial exposure of a biologic event to the various excitation bands with no external hardware beyond the light engine itself.

Stability

Because a light pipe based light engine is based on solid state technologies, they are extremely stable both in short duration experiments and over long term use. FIG. 4 depicts this stability. Light engines are powered by 24 V power supplies operated in DC mode, therefore there is no 60 Hz noise. All colors perform similarly. In 24 hours of continuous operation, the output fluctuates on the order of 1%. Short term stability on the order of 1.0 ms is approximately 0.5%. Short term stability for 0.1 ms is diminished by a factor of ten to 0.05%.

Eight Color Light Engine Subsystem

FIG. 5 shows a schematic for a eight color light engine layout. In an embodiment of the invention, a eight color light engine 500 includes a luminescent rod 502 and five other solid state light sources 504, with dichroic mirrors 506 to create a single coaxial 8-color beam 508 (for example selected from UV 395, Blue 440, Cyan 485, Teal 515, Green 550 or 575, Orange 630 and Red 650 nm) leading to an output 510. Each individual light source is collimated so as to be efficiently combined and after color combination, the beam is refocused into a light guide for transport to the device or system to be illuminated according to an embodiment of the invention. In this embodiment, a manual or electromechanical filter slider 512 allows green yellow filtering of YAG generating 550 or 575 nm light. Additional colors can be used. For example, a color band centered at 550 nm can be replaced with a color band centered at 560 nm. Each individual light source is collimated so as to be efficiently combined and after color combination, the beam is refocused into a light guide for transport to the device or system to be illuminated according to an embodiment of the invention.

The light engine subsystem is designed to interface to the array of bioanalytical tools with the expectation that the end user can take for granted the high quality of the illumination. Table IV summarizes four bioanalytical applications for which light engines including light pipes could replace more traditional illumination subsystems and offer performance and cost advantages. For example, Kohler illumination in transmitted light microscopy requires that the light be focused and collimated down the entire optical path of the microscope to provide optimal specimen illumination. Even light intensity across a fairly large plane is a critical requirement. For stereomicroscopy, lighting is achieved with ring-lights at the objective and fiber optic lights pointed at the specimen from the side. In both cases, the light engine must efficiently couple to a fiber optic cable.

For portable diagnostic tools, the delivery optics must provide even illumination over a small volume. These requirements are similar to, but less restrictive than those presented by capillary electrophoresis. Capillary electrophoresis requires an intense (10 mW) light focused onto the side of a capillary tube with characteristic dimensions on the order of a 350 pm outer diameter and a 50 pro inner diameter. To achieve this goal, the delivery optics were comprised of a ball lens to collect and collimate light from the lamp module (already coupled into an optical fiber), a bandpass filter to provide a narrow bandwidth of illumination, and an aspheric lens to focus the light at the center of the capillary bore. This approach yielded an 80 pin spot size and the desired 10 mW of delivered power to the capillary tube.

The design of delivery optics for microfluidic immunoassays requires both the even illumination required for optical microscopy and the small volume illumination required for capillary electrophoresis. Light engines capable of delivering even illumination at the active sites in a microfluidic array for detection of fluorescent tagged biomarkers have been designed for immunochemical as well as genomic applications. The advantages of the luminescent light pipe are providing commercial, readily available light engine solutions for illumination-detection platforms optimized for portable diagnostic tools.

Solid State Source of Continuous White Light

Figure 6B:
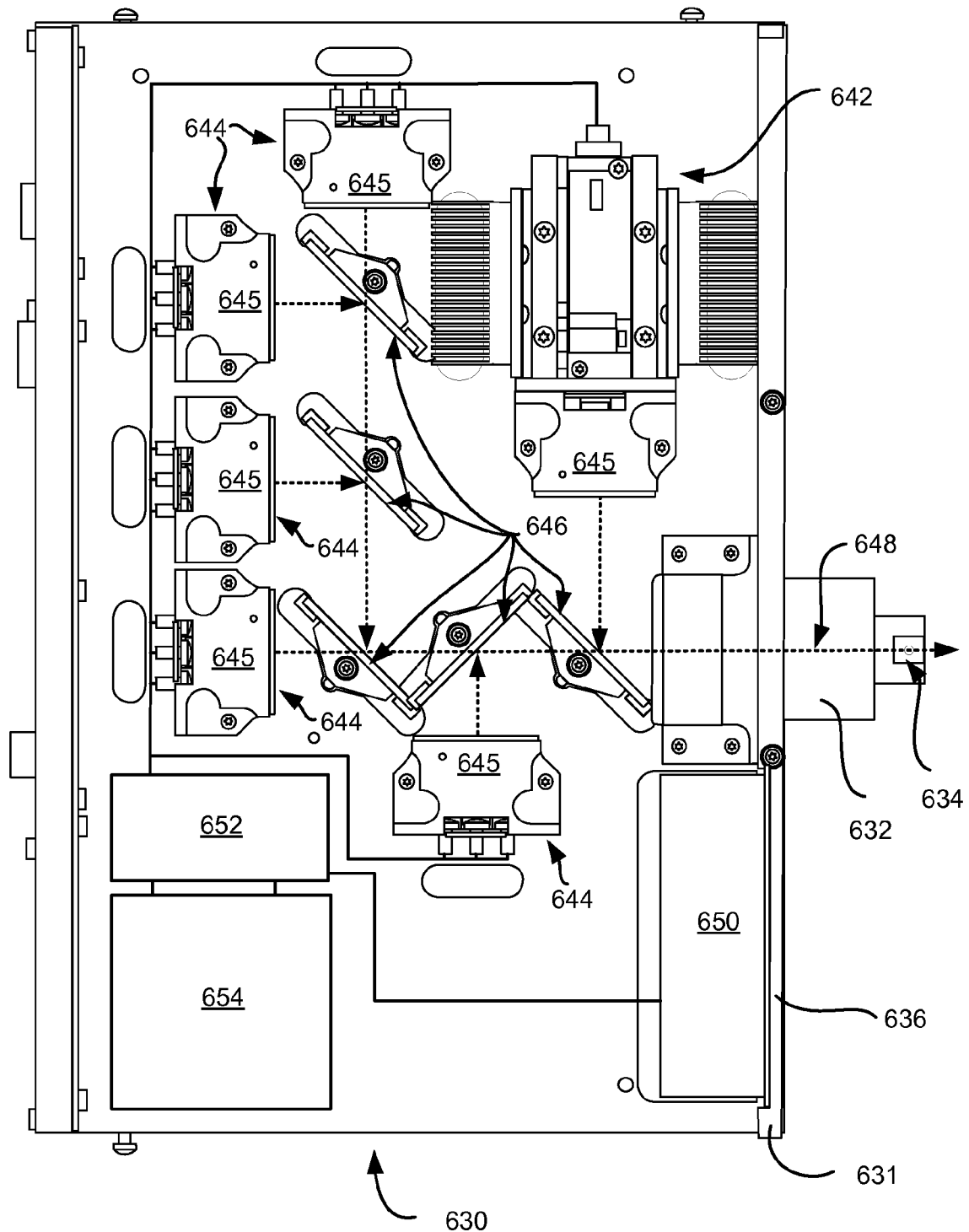
FIG. 6B shows a plan view of the components of the solid state white light subsystem of the white light illumination system of FIG. 6A.
Figure 6C:
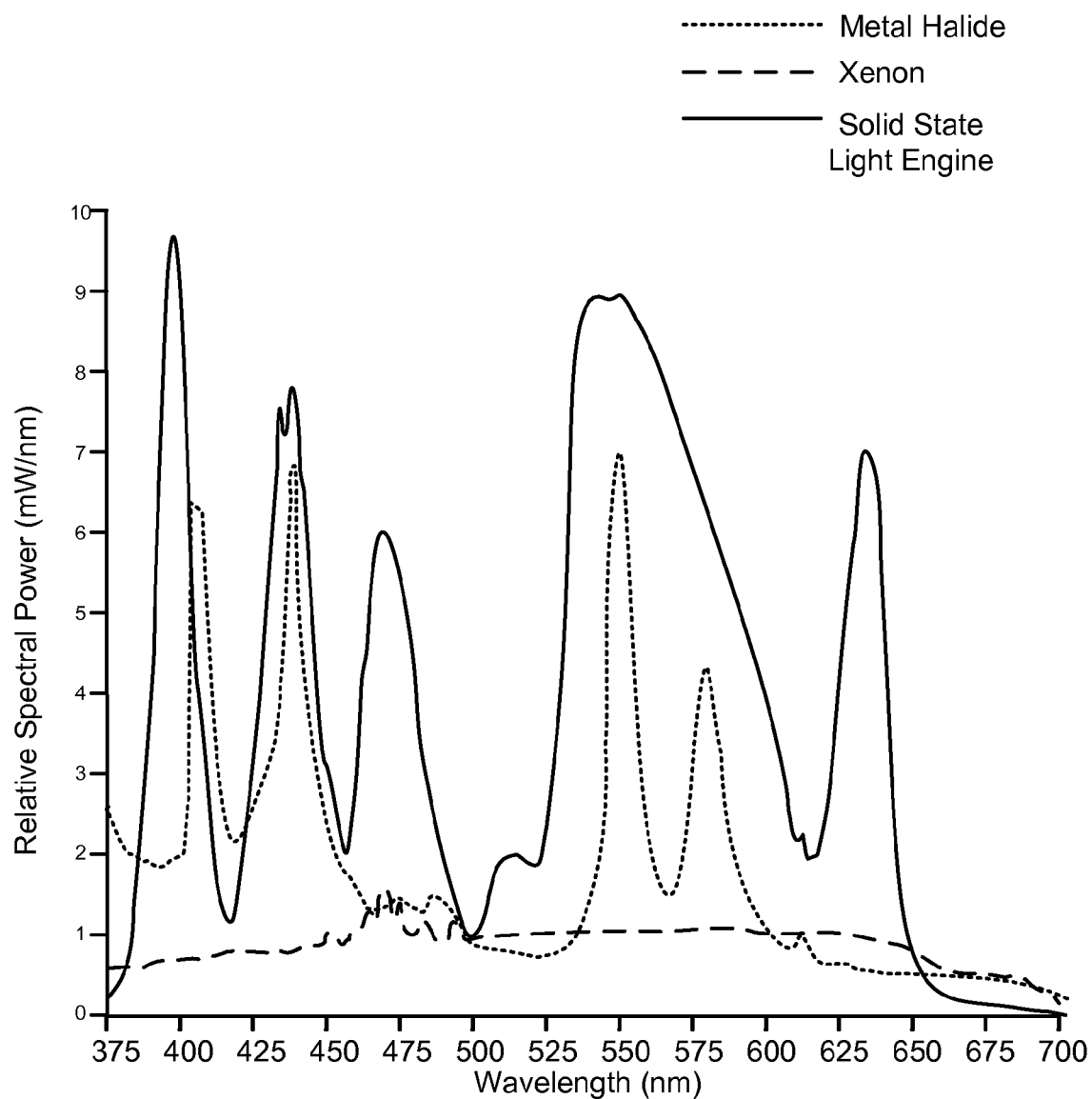
FIG. 6C is a graph showing spectral power of the solid state white light subsystem of FIG. 6B in comparison to a 120 W metal halide lamp and a 175 W Xenon lamp.

FIGS. 6A-6C shows aspects of a solid state illumination system 600 suitable for use as a replacement for conventional arc light, Metal Halide and Xenon white-light sources for applications in microscopy, fluorescence microscopy. The solid state illumination system utilizes multiple solid state light sources operating simultaneously to generate one white light output. The solid state illumination system 600 generates white light which is continuous in the visible spectrum from 380 nm to 650 nm, has a high color rendering index, including ultraviolet, and is suitable for imaging all the most common fluorophores and fluorescent proteins. The white light can be modulated using external bandpass filters.

In a preferred embodiment the total output power is approximately 2.5 W. Advantageously, the spectral power of the solid state illumination system 600 is equal to or greater than the spectral power of a 120 W metal halide lamp or 150 W Xenon lamp across substantially the entire visible spectrum from 380 nm to 650 nm. This solid state light source of the present invention is substantially different that prior art devices for microscopy that provide light of a selected color

TABLE IV

Performance and cost analysis of the light pipe engine vs. traditional illumination subsystems in four key bioanalytical applications

| specification | Sanger Sequencing | | Q-PCR | | Flow Cytometry | | Fluorescence Microscopy | |
|---|---|---|---|---|---|---|---|---|
| Light engine | Light Pipe | Ar Ion Laser | Light Pipe | Metal Halide | Light Pipe | Lasers | Light Pipe | Metal Halide |
| Intensity W/cm$^2$ | 150-250 | 150-250 | 0.5-1 | 0.2-1, very λ specific | 150-250 | 150-250 | <50 | 1-50, very λ specific |
| Wavelength | 505 nm | multiline | 4 colors | | >2 colors | | 4 colors | |
| Bandwidth, nm | 10-30 | 26 | 10-30 | 15 | 10-30 | <5 | 10-30 | 15 |
| Stability | 0.1% | >1% | 0.1% | >1% | 0.1% | >1% | 0.1% | >1% |
| Switching, ms | <0.03 | 1-10, ext. shutter | <0.03 | 40, ext. shutter | <0.03 | 1-10, ext. shutter | <0.03 | 40, ext. shutter |
| MTBF, hrs | >10,000 | <4,000 | >10,000 | <1,000 | >10,000 | <4,000 | >10,000 | <1,500 |
| Price | <$3K | >$5K | <$7.5K | >$10K | <$5K | >$5K | <$7.5K | >$10K | for microscopy rather than providing continuous spectrum white light which can be externally filtered downstream—for example using filter systems previous only suitable for arc lamps—thus the user can utilize a broad range of commercially available filters. This provides the most flexibility to the user in utilizing the light output.

FIG. 6A shows the solid illumination system 600; FIG. 6B shows a plan view of the components of the solid state light engine 630 of the solid state illumination system of FIG. 6A; and FIG. 6C is a graph showing spectral power of the solid state light engine of FIG. 6B in comparison to a 120 W metal halide lamp and a 175 W Xenon lamp. Referring first to FIG. 6A which shows solid state illumination system 600. As shown in FIG. 6A, solid state illumination system 600 includes a flexible fiber optic 610, a filter system 620, and a solid state light engine 630. Solid state light engine 630, includes a liquid light guide 632 mounted on the exterior of housing 631 of solid state light engine 630. Liquid light guide 632 includes an aperture 634 through which white light is provided from solid state light engine 630. Liquid light guide 632 includes a coupling for connecting external filter system 620 and/or flexible fiber optic 610 to solid state light engine 630 such that white light from aperture 634 is efficiently coupled to external filter system 620 and/or flexible fiber optic 610. A grill 636 allows flow of air through housing 631 for cooling the light sources.

Filter system 620 includes one or more light filters 622 which can be placed in the path of the white light exiting from aperture 634. As shown in FIG. 6A, filter system 620 includes a slot 624 designed to receive a filter paddle 623 holding a light filter 622. A range of filter paddle/filter combinations is provided in order that a user can modify the white light according to the users needs. Alternatively, an automated and/or computer controlled filter system can be utilized. For example a motorized filter wheel including a plurality of different filters can be used—a controller allows the selection and positioning of the desired filter in the light path. Alternatively, in some embodiments filter system 620 can comprise a filter cube including a dichroic mirror mounted on an optical block for use in florescence microscopy. Such filter cubes are typically mounted directly to the microscope rather than the solid state light engine 630. Advantageously, by providing continuous white light as an output the solid state light engine 630 allows for the use of conventional filter systems utilized with arc lamps.

Flexible fiber optic 610 is used to connect solid state light engine 630 to an optical system such as a microscope or endoscope. Adapters are provided to connect flexible fiber optic 610 to a range of microscope, endoscope and/or other desired optical systems requiring illumination. Flexible fiber optic 610 transmits light from solid state light engine 630 along its length to the optical system through optical fibers and or a liquid medium. Flexible fiber optic 610 is in some case connected between solid state light engine 630 and filter system 620 (for example where filter system 620 is mounted directly to a microscope. In other cases, flexible fiber optic 610 is connected to a coupling of filter system 620 as shown in FIG. 6A.

The light engine subsystem is designed to interface to the array of bioanalytical tools with the expectation that the end user can take for granted the high quality of the illumination. Table IV (above) summarizes four bioanalytical applications for which light engines including light pipes could replace more traditional illumination subsystems and offer performance and cost advantages. For example, Kohler illumination in transmitted light microscopy requires that the light be focused and collimated down the entire optical path of the microscope to provide optimal specimen illumination. Even light intensity across a fairly large plane is a critical requirement. For stereomicroscopy, lighting is achieved with ringlights at the objective and fiber optic lights pointed at the specimen from the side. In both cases, the light engine must efficiently couple to a fiber optic cable and thence to the particular bioanalytical tool.

FIG. 6B shows a plan view of the components of the solid state light engine 630 of the solid state illumination system. As shown in FIG. 6B, housing 631 contains a light pipe engine 642, and five LED light sources 644, and a plurality of dichroic mirrors 646. Each individual light source is collimated so as to be efficiently combined and after color combination, the beam is refocused into a light guide for transport to the device or system to be illuminated. The light pipe engine 642 and the LED light sources 644 each include output optics 645 to image and collimate the light output of the source into a beam that can be imaged on the input aperture of the liquid light guide 632. The light pipe engine 642, the LED light sources 644, and dichroic mirrors 646 are arranged to create a single coaxial light beam 648 which is directed at the input aperture of the liquid light guide 632 as shown by the dashed arrows. In a preferred embodiment, the light beam 648 output is white light which is substantially continuous over the visible spectrum of 380 nm-680 nm and includes no ultraviolet or infrared light.

Housing 631 also contains a fan 650, controller 652, and power supply 654. Housing 631 can also contain one or more sensors (not shown) to analyze the spectral content of light beam 648. Power supply can be an AC/DC transformer for wired applications or may alternatively be a battery for portable applications.

LED light sources 644 and light pipe engine 642 are selected to provide different color components of the spectral content of the continuous white light output. In a preferred embodiment there are five LED light sources 644 each producing a different color component of the continuous white light output. The output wavelengths of the sources overlap and combine to some extent contributing the overall spectral output of the solid state light engine 630. The LED light sources are ganged together and with the light pipe engine 642. In embodiments the LED light sources 644 and light pipe engine 642 produce spectral components centered on colors violet 395 nm, blue 425-460 nm, cyan 460-500 nm, teal 515 nm, green 500-615 nm, and red/orange 615-685 nm. All of LED light sources 644 and light pipe engine 642 are turned on at the same time such that the different colors are combined to create a substantially continuous white light having a high color rendering index (CRI). In alternative embodiments, a second light pipe engine 642 can be used in place of one or more of the direct LED light sources 644.

In a preferred embodiment light pipe engine 642 is used to generate green (green and yellow) light spanning 500-600 nm. LED lights that emit green light at high power are notoriously difficult to create—the so-called green gap. Thus light pipe engine 642 utilizes high power blue LED light sources to excite a luminescent rod which emits green light spanning 500-600 nm. In a preferred embodiment light pipe engine utilizes two arrays of 40 blue LEDs to excite emission of green light from the luminescent rod. A suitable light pipe engine 100 is described above with respect to FIG. 1. Suitable light engines are also described in the Related Applications listed above and incorporated herein by reference. The luminescent rod of the light pipe engine can be convectively cooled as previously described or conductively cooled by being clamped into contact with a metal pedestal heat sink (for example a copper heat sink.) A light pipe engine operating to generate green light allows the solid state light engine 630 to produce an output in the green and amber bands that is the same or greater than commonly used arc lamps (see, e.g. FIG. 6C). Thus, no compromise in output power, even for the 546 nm band of the arc lamp, is be incurred as a consequence of using solid state light engine 630 as a replacement for an arc lamp.

As shown in FIG. 6B controller 652 is connected to each of the LED light sources 644 and light pipe engine 642. In a preferred embodiment, control of all of LED light sources 644 and light pipe engine 642 is ganged. For example, each of the LED light sources 644 and light pipe engine 642 is turned on and off at the same time and the power of each of the LED light sources 644 and light pipe engine 642 is modulated in the same way. Thus if one LED light source is dimmed by 50% all of the LED light sources 644 and light pipe engine are dimmed by 50%. To put it another way, as the light output of the preferred embodiment is desired to be white light, the LED light sources 644 and light pipe engine cannot be independently turned off an on or independently adjusted in power output. To the extent that a user desires to alter the spectral content of the white light, the user is required to modulate the white light with filters placed in the light beam 648. Typically this is done using external bandpass filters in filter system 620.

Controller 652 communicates with software, cameras, microscopes, remote controls, and/or foot pedals to allow control of solid state light engine 630. For example in a preferred embodiment UNIBLITZ® command control is supported for on/off synchronization in place of an electronic shutter. For additional example, a remote control accessory can be used to facilitate control by allowing user operation without a dedicated computer or third party software. A remote control accessory can be compatible with 3rd party software control of the illuminator but simplifies light engine operation and reduces start up time. A camera interface provides exact synchronization in a complete imaging system. The camera interface to controller 652 eliminates lag time, minimizes photo-damage to sensitive samples, and ensures exposure of biological samples to only the required amount of light needed for a given experiment.

Because solid state light sources are used, the light engine can be turned on and off at a high switching speed not possible with arc lamps. For example, in an embodiment, the switching speed can be up to 5 kHz with turn on/off in approximately 10 µs. The high switching speed enable light blanking during frame readout thereby minimizing photobleaching during sample illumination and prolonging sample life. The short warm-up time of the system and superior stability of the solid state light sources provide for highly reproducible output power as well as a long expected lifetime greater than 15,000 hours without the need for arc lamp alignment, installation and replacement. Moreover, the solid state light engine also produces less heat, thus reducing the power and cooling requirements of the system as compared to arc lamp systems.

FIG. 6C is a graph showing spectral power of the solid state light engine of FIG. 6B in comparison to commonly used 120 W metal halide lamps and a 175 W Xenon lamps. As shown in FIG. 6C, the solid state light engine 630 generates white light which is continuous in the visible spectrum from 380 nm to 650 nm and is suitable for imaging all the most common fluorophores and fluorescent proteins. Advantageously, the spectral power of the solid state illumination system 600 is equal to or greater than the spectral power of a 120 W metal halide lamp or 150 W Xenon lamp across substantially the entire visible spectrum from 380 nm to 650 nm. In particular embodiments the spectral power is greater than 1 mW/nm over the substantially the entire visible spectrum from 380 nm to 650 nm and greater than 3 mW/nm over the range from 500-600 nm. The continuous white light provided solid state light engine 630 provides white light having a high color rendering index. Moreover, the color temperature, and other attributes of the white light can readily be modulated with external filters in filter system 620. Thus solid state light engine 630 can serve as a direct replacement for 120 W metal halide lamp or 150 W Xenon lamps.

In alternative embodiments, controller 652 can be designed to control LED light sources 644 and light pipe engine 642 individually (on/off and intensity) such that the spectral content of the output light can be modulated and/or changed in color. Moreover, in an alternative embodiment, filter system 620 can be integrated into housing 631 such that filters 622 can be inserted into the output light path manually (for example through a slot in the housing) or under the control of controller 652 (for example a motorized-controlled filter wheel).

The foregoing description of the various embodiments of the present invention has been provided for the purposes of illustration and description. It is not intended to be exhaustive or to limit the invention to the precise forms disclosed. Many modifications and variations will be apparent to the practitioner skilled in the art. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

Solid State Illumination System

FIGS. 7A-7E shows aspects of a solid state illumination system 700 suitable for use as a replacement for conventional arc light, Metal Halide and Xenon white-light sources for applications in microscopy, fluorescence microscopy, and endoscopy. The solid state illumination system includes multiple solid state light sources operating simultaneously to generate white light output or operating separately to provided light of a desired spectral distribution. When generating white light, the solid state illumination system 700 generates white light which is continuous in the visible spectrum from 380 nm to 650 nm, has a high color rendering index, and is suitable for microscopic and endoscopic imaging. The solid state illumination engine 700 includes two solid state laser light sources which provide coherent light having selected wavelengths. Features of the solid state illumination system include: powerful white light for high-definition (HD) visible illumination and imaging; controllable color spectrum for high contrast imaging matched to color cameras; narrowband light for indocyanin green (ICG) excitation, endogenous fluorescence, other imaging agents; simultaneous illumination of white light and fluorescence images; spectral stability (<1% drift, usage dependent) & power stability (5 kHz with turn on/off ~10 µs); illumination uniformity; microsecond switching with no filters or shutters (≥5 kHz modulation, ≤6 is rise time, ≤20 is fall time); minimal heat generation; computer control; long life >10,000 hours with no consumable parts; short warm up time (1-10 minutes); and a compact size (9×18×23 cm) for off-the-shelf and custom OEM configurations. Options include a customizable Wavelength range tailorable from visible to NIR; customizable maximum and minimum light optical power per application; customizable optical interface adapted e.g. for optical fibers, fiber bundles, liquid light guides; customizable complete computer control interface via e.g. RS-232, TTL and USB; and a dosimeter for realtime instantaneous power monitoring.

The solid state illumination system 700 is designed to interface to the array of bioanalytical tools with the expectation that the end user can take for granted the high quality of the illumination. Table IV (above) summarizes four bioanalytical applications for which light engines including light pipes could replace more traditional illumination subsystems and offer performance and cost advantages. For example, Kohler illumination in transmitted light microscopy requires that the light be focused and collimated down the entire optical path of the microscope to provide optimal specimen illumination. Even light intensity across a fairly large plane is a critical requirement. For stereomicroscopy, lighting is achieved with ring-lights at the objective and fiber optic lights pointed at the specimen from the side. In both cases, the light engine must efficiently couple to a fiber optic cable and thence to the particular bioanalytical tool.

In a preferred embodiment the total optical output power is approximately 2.5 W. Advantageously, the spectral power of the solid state illumination system 700 is equal to or greater than the spectral power of a 120 W metal halide lamp or 150 W Xenon lamp across substantially the entire visible spectrum from 380 nm to 650 nm. If needed, the user can utilize a broad range of commercially available filters. This provides the most flexibility to the user in utilizing the light output. The solid state illumination system 700 includes an adapter for coupling the output of solid state illumination system 700 into a light guide, for example a liquid light guide or fiber optic light guide for transmission to an endoscope or microscope.

The cooling requirements for a solid state illumination system are substantially different than that for an incandescent light source. Incandescent lights typically release 90% or so of the heat they generate to their environment through radiation in the infrared and less than 10% through conduction. In comparison, LEDs typically release 90% or so of the heat they generate to their environment through conduction and less than 10% through conduction. Thermal dissipation is a key factor that limits the power output of an LED light source. Even though LEDs bulbs are considerably more efficient at converting electrical energy into light than incandescent light sources, but the LED components and the driver electronics can still create a considerable amount of heat. If this heat is not dissipated properly, the LED's quality of light, emission spectra, and life expectancy decrease dramatically. Thus, it is important in a solid state illumination system relying on LEDs to provide a solution for conductive cooling of the LEDs.

Figure 7A:
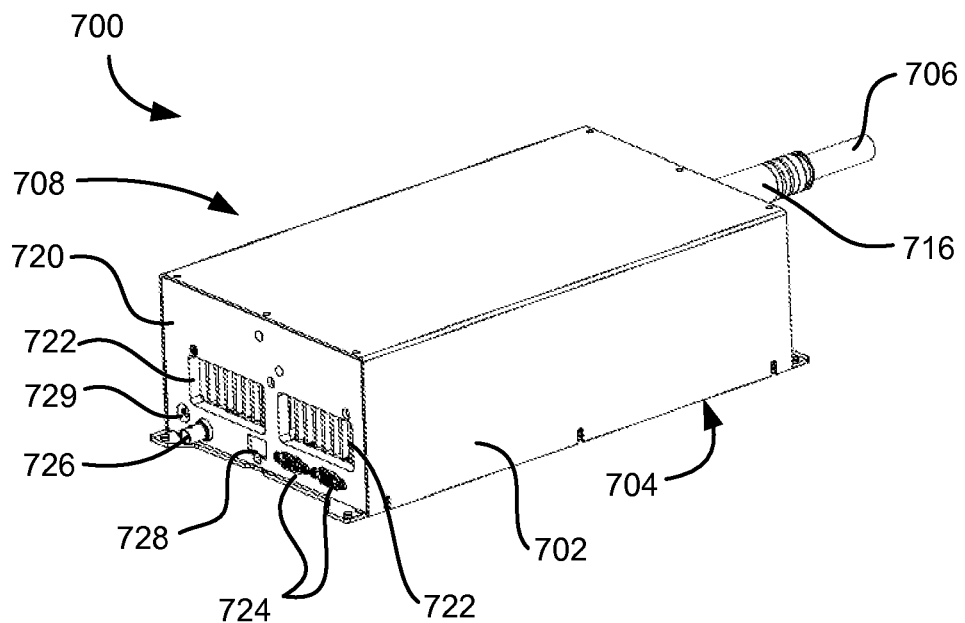
FIGS. 7A and 7B show external views of a solid state illumination system according to an embodiment of the present invention.
Figure 7B:
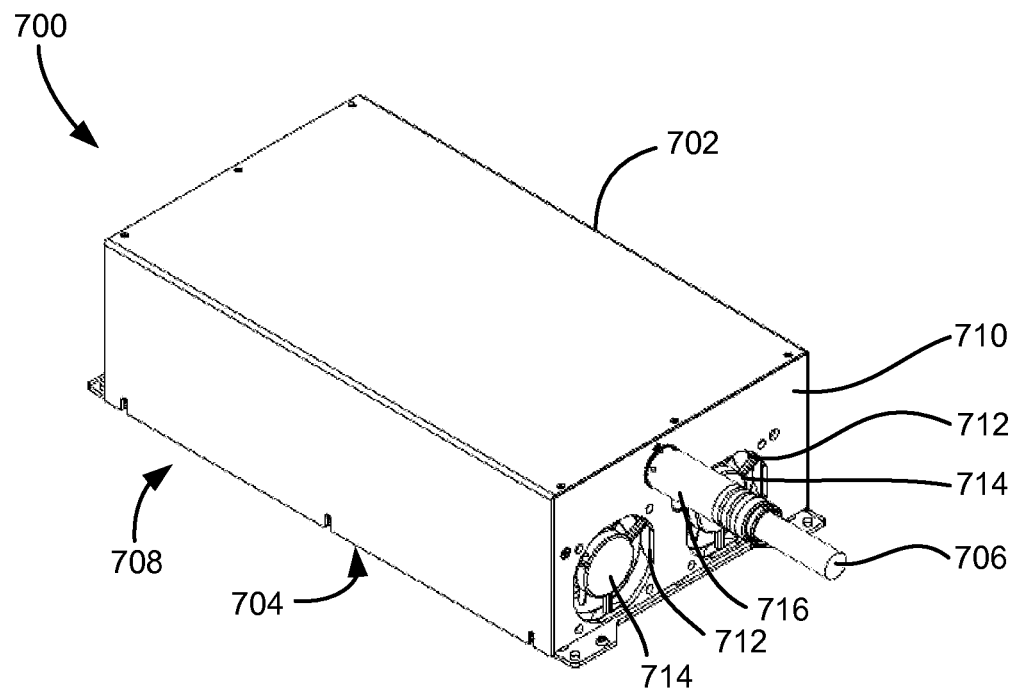
Figure 7C:
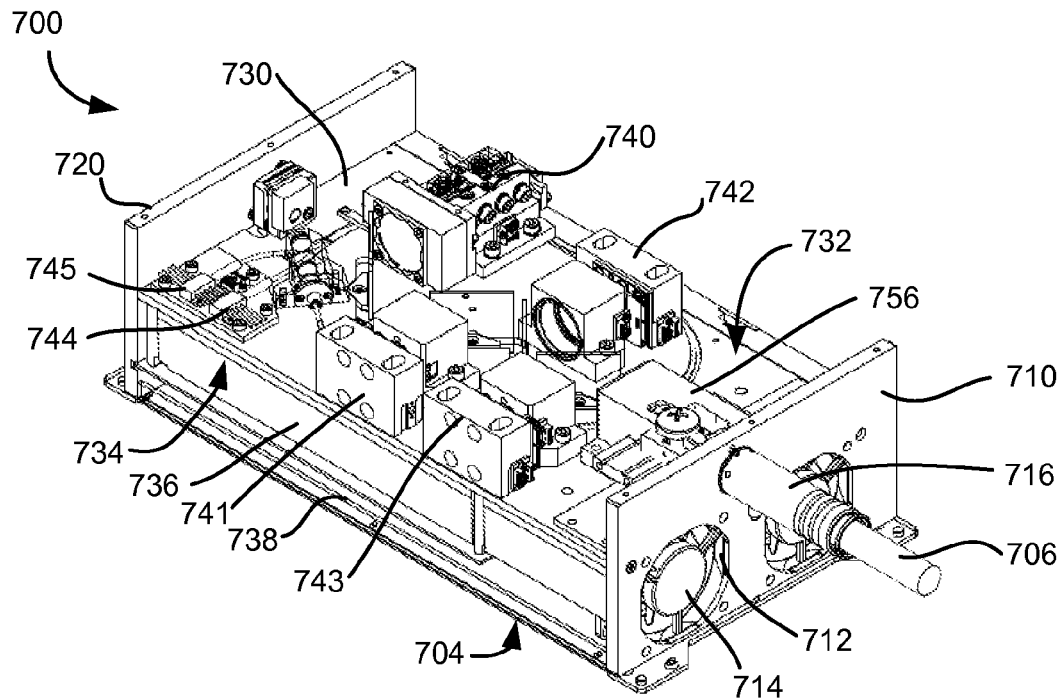
FIG. 7C shows an internal perspective view of the solid state illumination system of FIGS. 7A and 7B.
Figure 7D:
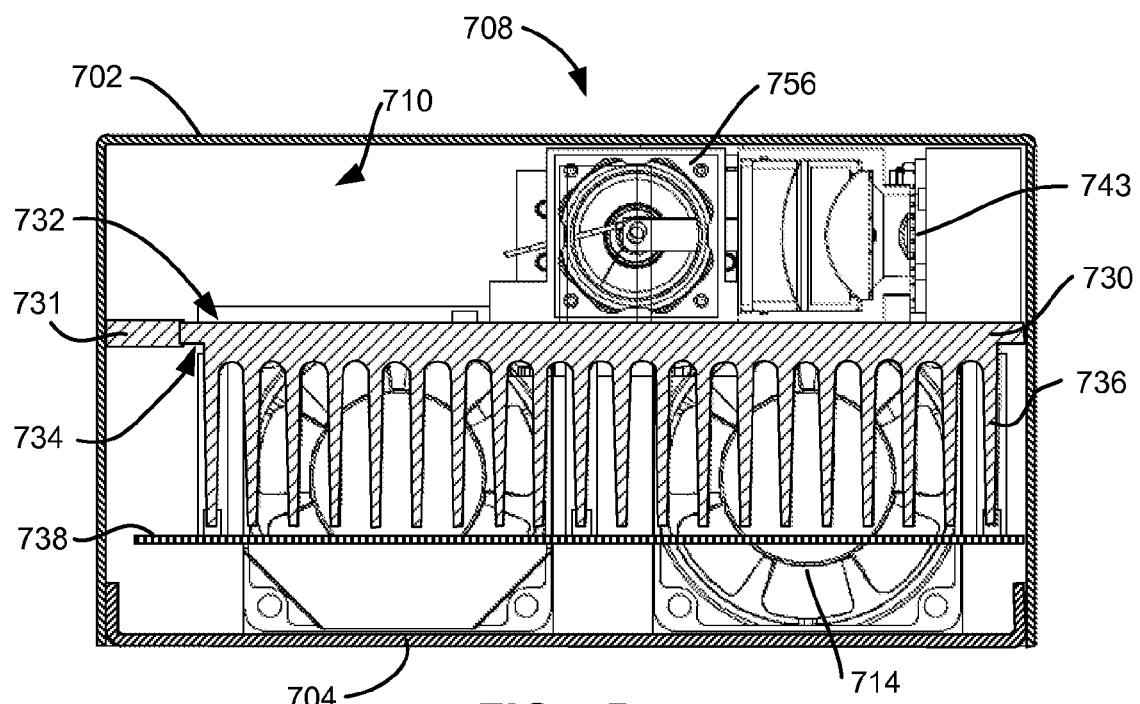
FIG. 7D shows a sectional view of the solid state illumination system of FIGS. 7A and 7B.
Figure 7E:
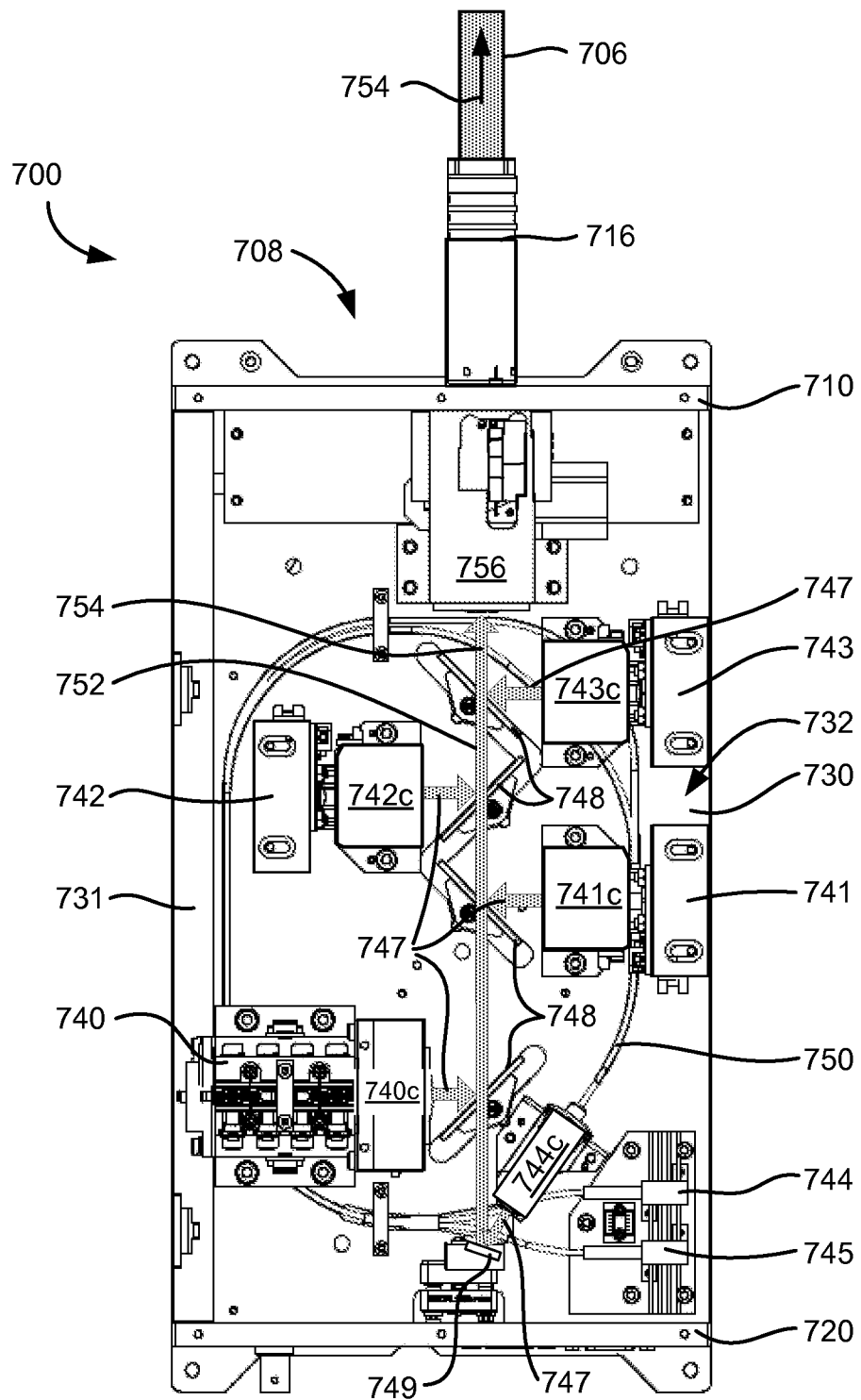
FIG. 7E shows an internal plan view of the solid state illumination system of FIGS. 7A and 7B.

FIGS. 7A and 7B show exterior perspective views of the solid state illumination system 700; FIG. 7C shows an internal perspective view of the solid state illumination system 700. FIG. 7D shows a sectional view of the solid state illumination system 700. FIG. 7E shows a top view of the optical components of the solid state illumination system 700.

Referring first to FIGS. 7A and 7B which show exterior perspective views of solid state illumination system 700. Solid state illumination system 700 is enclosed by a 3-sided cover 702, front plate 710, back plate 720 and base plate 704. 3-sided cover 702, front plate 710, back plate 720 and base plate 704 together comprise a housing 708 which protects the solid state illumination system 700 and substantially prevents the entry/exit of light, and air except as provided. Front plate 710 includes two apertures 712 through which two fans 714 draw air for cooling the solid state illumination system 700. Front plate 710 also supports an adapter 716 which accepts a light guide 706 which may be a liquid light guide or fiber optic light guide. Back plate 720 includes two apertures 722 through which the cooling air exits the solid state illumination system 700. Back plate 720 also bears computer control ports 724, shutter control port 726 and power port 728 and switch 729.

FIG. 7C, shows an internal perspective view of the solid state illumination system 700 with the 3-sided cover 702 removed. As shown in FIG. 7C, the interior of solid state illumination system 700 is divided by a platform 730. The top surface 732 of platform 730 is substantially flat and supports the solid state light sources and associated optics. The bottom surface 734 of platform 730 bears a plurality of fins 736 which provided a large surface area for the cooling of platform 730. The fins are arranged parallel to the axis of the air flow from the front plate 710 to the back plate 720. Platform 730, maintains the cooling air flow from fans 714 in the lower portion of housing 708 between base plate 704 and platform 730. This prevents cooling air flow from fans 714 around the solid state light sources and associated optics reducing the possibility of contamination of the optical components. Control board 738 sits between platform 730 and base plate 704 such that it also receives cooling air flow from fans 714. Control board 738 includes the circuitry for driving the solid state light sources, shutter and sensors of solid state illumination system 700.

FIG. 7D shows a sectional view through solid state illumination system 700 looking towards front plate 710 and fans 714. As shown in FIG. 7D, fans 714 direct cooling air only through the lower portion of housing 708 between the lower surface 734 of platform 730 and base plate 704. The cooling air is directed past fins 736 on the lower surface 734 of platform 730. The cooling air is directed past both sides of control board 738. Cooling air is not circulated above platform 730 among the solid state light sources and associated optics. Note that in the embodiment shown, platform 730 includes a platform extension 731 which extends platform 730 the full width of housing 708. In alternative embodiments platform 730 is formed in one piece and extends the full width of housing 708.

FIG. 7E shows a top of the solid state illumination system 700 with the 3-sided cover 702 removed. FIG. 7E shows the layout of the solid state light sources and associated optics on the top surface 732 of platform 730. In the embodiments of solid state illumination system 700, the solid state light sources include a light pipe engine 740, three LED light sources 741, 742, 743, and two solid state laser light sources 744, 745. The light pipe engine 740 and three LED light sources 741, 742, and 743 emit non-coherent light of different colors. The LED light sources 744, 745 emit coherent light in different narrow band wavelengths. Each of the light sources includes a collimator 740c, 741c, 742c, 743c which forms the light output from the source into a collimated beam 747. The solid state laser light sources 744, 745 are coupled to a single collimator 744c by an optical fiber 750. Each of the light sources is aligned with a dichroic mirror 748 at which the collimated light beam 747 is directed. The dichroic mirrors 748 are aligned so as to combine the collimated beams 747 onto a single optical axis 752 generating a combined coaxial beam 754 aligned with output optics 756. Output optics 756 focus the combined beam 754 into light guide 706 positioned within adapter 716. Light guide 706 transmits the combined beam 754 to a microscope or endoscope.

Light pipe engine 740, three LED light sources 741, 742, 743, and two solid state laser light sources 744, 745 are selected to provide different color components of the spectral content of the light output. In a preferred embodiment the three LED light sources 741, 742, 743 each produce a different color component of the continuous light output. The output wavelengths of the sources overlap and combine to some extent contributing the overall spectral output of the solid state illumination system 700. In an alternative embodiment, one or more of light pipe engine 740, three LED light sources 741, 742, 743 is provided with a manual or electromechanical filter slider (see, e.g. 512 of FIG. 5) which filters and thereby adjusts the spectral content of the light from the light source prior to combination with the light from the other sources. The LED light sources and the light pipe engine are controlled by the controller board 738 either together or individually to control the spectral content of the output beam. In embodiments the light pipe engine 740 and three LED light sources 741, 742, 743 produce spectral components centered on colors violet 395 nm, blue 425-460 nm, cyan 460-500 nm, teal 515 nm, green 500-615 nm, and red/orange 615-685 nm. All of light pipe engine 740 and three LED light sources 741, 742, 743 can be turned on at the same time such that the different colors are combined to create a substantially continuous white light having a high color rendering index (CRI). In alternative embodiments, a second light pipe engine can be used in place of or in addition to the three LED light sources 741, 742, 743. In a preferred embodiment light pipe engine 740 is used to generate green (green and yellow) light spanning 500-600 nm.

As previously described the cooling air from fans 714 is not circulated in the upper portion of housing 708. However, the solid state light sources including light pipe engine 740, three LED light sources 741, 742, 743, and two solid state laser light sources 744, 745 generate a heat during operation. This heat must be removed such that the temperature of the solid state light sources is maintained at a desired level. In prior devices, the individual solid state light sources were provided with individual finned heat sinks and air was passed over the heat sinks using a common or individual fan to remove heat—however, this cooling system allowed for the entry of dust and/or other contaminants into the light sources and onto the optical components. The dust and/or other contaminants could cause a number of problems including: reduction in optical efficiency, scattering of light within housing 708, burning, and burning odor.

In the solid state illumination system 700 shown in FIGS. 7A-7E, each of the solid state light sources including light pipe engine 740, three LED light sources 741, 742, 743, and two solid state laser light sources 744, 745 is in thermal contact with platform 730. The thermal contact is direct metal to metal contact or may be mediated by a thermal paste between the solid state light source and the platform 730. Platform 730 is made from a conductive metal/metal alloy such that head from the solid state light sources is rapidly conducted away towards fins 736 which are provided with cooling air by fans 714. Thus platform 730 serves both as an optical table for mounting and aligning the solid state light sources, mirrors and output optics as well as a common heat sinks for the solid state light sources including light pipe engine 740, three LED light sources 741, 742, 743, and two solid state laser light sources 744, 745. The solid state light sources are suitably designed to efficiently transmit heat from their components to the platform 730 as described with respect to FIGS. 8A-11D below. Light pipe engine 740, three LED light sources 741, 742, 743, and two solid state laser light sources 744, 745 are arranged on the platform based upon their heat output for example in an embodiment, light pipe engine 740 puts out 100 Watts of heat whereas LED light sources 741, 742, 743 put out 25 Watts of heat each. Thus, the thermal output of the light sources is considered when arranging the light sources to ensure that each is adequately cooled by the cooling airflow on the finned side of platform 730.

Figure 7F:
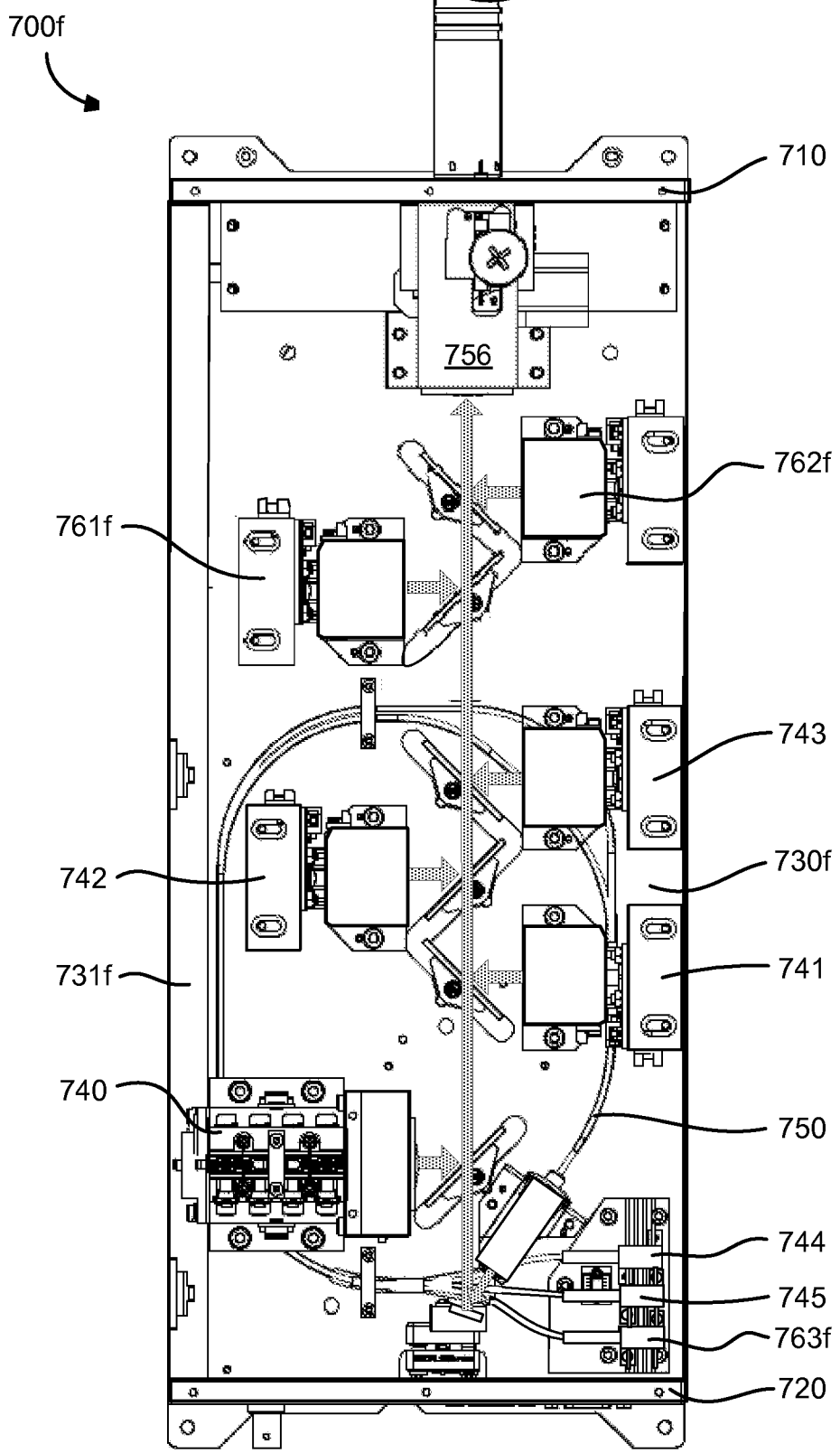
FIG. 7F shows an internal plan view of a variation of the solid state illumination system of FIGS. 7A and 7B.

FIG. 7F illustrates a variation 700f of the solid state illumination system 700 of FIGS. 7A-7E. As shown in FIG. 7F additional light sources can be added to the solid state illumination system by using a platform 730f and platform extension 731f (the cover and base—not shown—should also be increased in length. The increase in the length of platform 730f allows for the inclusion of two additional light sources 761f, 762f which preferably emit light having a different wavelength than the other light sources. In an alternative embodiment, an additional light pipe engine 740 is positioned on the extended length platform 730f. Note also that an additional laser light source 763f has been added. Laser light sources 744, 745, 763f are relatively small that it is possible to include a variety of laser light sources emitting different wavelengths of coherent light such that a user can selectively activate those laser light sources suitable for a particular application. The solid state illumination system 700f can provide up to six colors of non-coherent light and up to three colors of coherent light. Note that in some embodiments two or more light sources or laser light sources can produce the same color of light in order to increase the intensity of such color available.

Figure 7G:
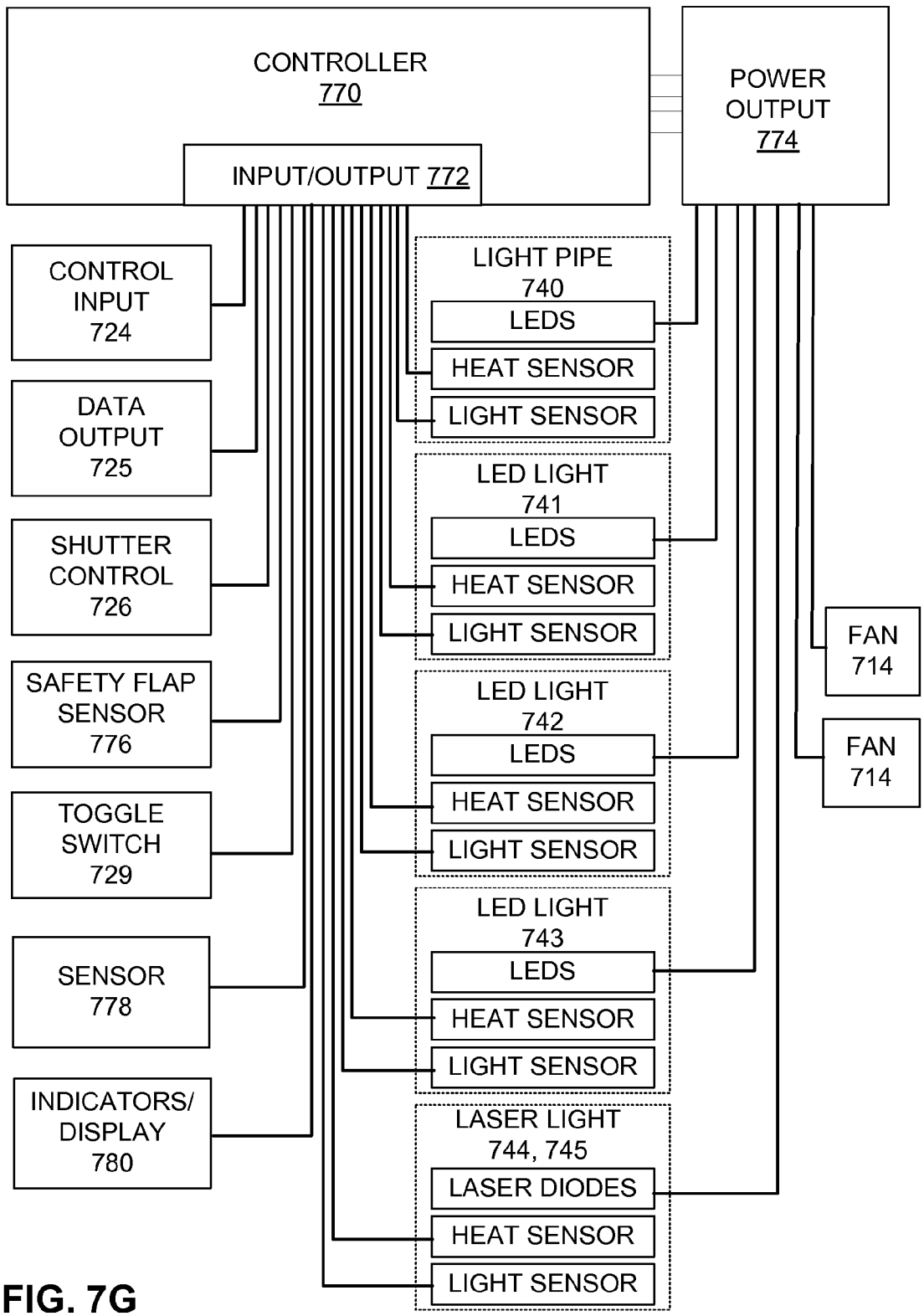
FIG. 7G illustrates a block diagram of a control system of the solid state illumination system of FIGS. 7A to 7F.

FIG. 7G illustrates a control system of the solid state illumination system 700 of FIGS. 7A and 7B. As shown in FIG. 7G, control board 738 see FIGS. 7C, 7D includes a controller 770. Controller 770 includes an input/output system 772 for receiving data from the various sensors, input port and input devices and sending data to the data output port and or any indicator/display devices. Controller 770 is coupled to power output system 774 which provides power to the electrical, optical and mechanical components of solid state illumination system 700. Because of the solid state nature and independently operable designs of the light sources, coupled to fast (approximately 10 ns) decay times of typical materials employed, the solid state illumination system does not require a mechanical shutter and is capable of rise times of less than 20 μs and fall times of less than 2 μs (see, e.g. FIG. 3) under the control of controller 770 which is compatible with triggering by TTL, RS232 and USB and intensity control by RS232, USB or manually). Each light source is operated simultaneously to generate a continuous white light output. Alternatively, each source can be switched independently to generate an output of the desired spectral power distribution and/or color.

In the control system embodiment shown in FIG. 7G, controller 770 is coupled by input/output system 772 to control input port 724, data output port 725, shutter control port 726, safety flap sensor 776, toggle switch 729, additional sensor(s) 778, display/indicators 780, as well as the heat and light sensors of each light source, including light pipe engine 740, three LED light sources 741, 742, 743, and two solid state laser light sources 744, 745. Additional sensors 778, display/indicators 780 and inputs/switches and outputs may be added to solid state illumination system 700 as necessary to support desired functionality for the system, however, typically a computer connected to control input port 724 and data output port 725 is used to control and monitor solid state illumination system 700 and provides control and data display flexibility. Input and output can be provided, for example via TTL, RS232 and/or USB. Controller 770 is coupled to power output system 774 which provides electrical power to drive the LEDs and laser diodes of light pipe engine 740, three LED light sources 741, 742, 743, and two solid state laser light sources 744, 745. Power output system 774 is also coupled to fans 714 such that controller 770 can control the speed of fans 714 in order to control the temperature of solid state illumination system 700. The fan speed may be adjusted in response to temperature readings from the heat sensors of the various components of solid state illumination system 700. Fans 714 are, in some embodiments driven at different speeds to account for the different cooling requirements of the components cooled by air from the particular fan.

The solid state illumination system generates powerful, white and/or multi-color, stable, durable light. The illumination can be tuned to match any color temperature of interest. This is particularly important for minimally invasive surgery where RGCB components can be balanced for maximum signal/noise and contrast. Simultaneously, fluorophore excitation may be superimposed on the general field producing superior image quality as well as optical selectivity. In a typical embodiment, light pipe engine 740 produces 3.0 Watts of green light output (wavelength 500-615 nm); and LED light sources 741, 742, 743 produce 1.8 Watts of blue light output (wavelength 425-460 nm), 0.9 Watts of cyan light output (460-500 nm), and 1.8 Watts of red light output 615-685. All of light pipe engine 740 and three LED light sources 741, 742, 743 can be turned on at the same time such that the different colors are combined to create a substantially continuous white light having a high color rendering index (CRI). Solid state laser light sources 744, 745 can produce near infrared light for fluorescence excitation for example 6.0 W of narrowband red at 785-880 nm.

Figure 7H:
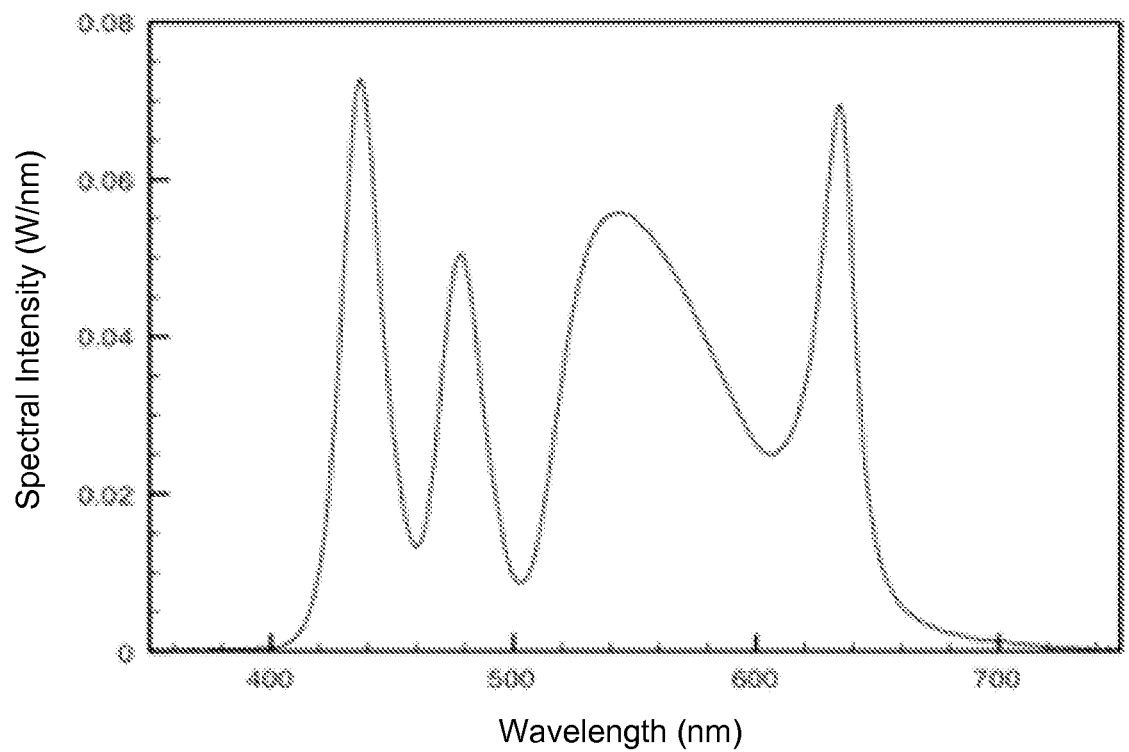
FIG. 7H illustrates the output spectra of one embodiment of the solid state illumination system of FIGS. 7A to 7E.

FIG. 7H illustrates the output spectra of one embodiment of the solid state illumination system of FIGS. 7A and 7B. As illustrated by FIG. 7H the solid state illumination system can produce powerful white light with any color temperature (red/green/cyan/blue, RGCB) alongside narrowband excitation for targeting fluorescence. The illumination system is powerful enough to yield high contrast, real-time imaging as well as to maximize fluorescence signals. The illumination system provides spectral, temporal and spatial control of light for surgical and non-surgical procedures. The stable, robust lighting enables long term monitoring and quantitation.

Figure 8A:
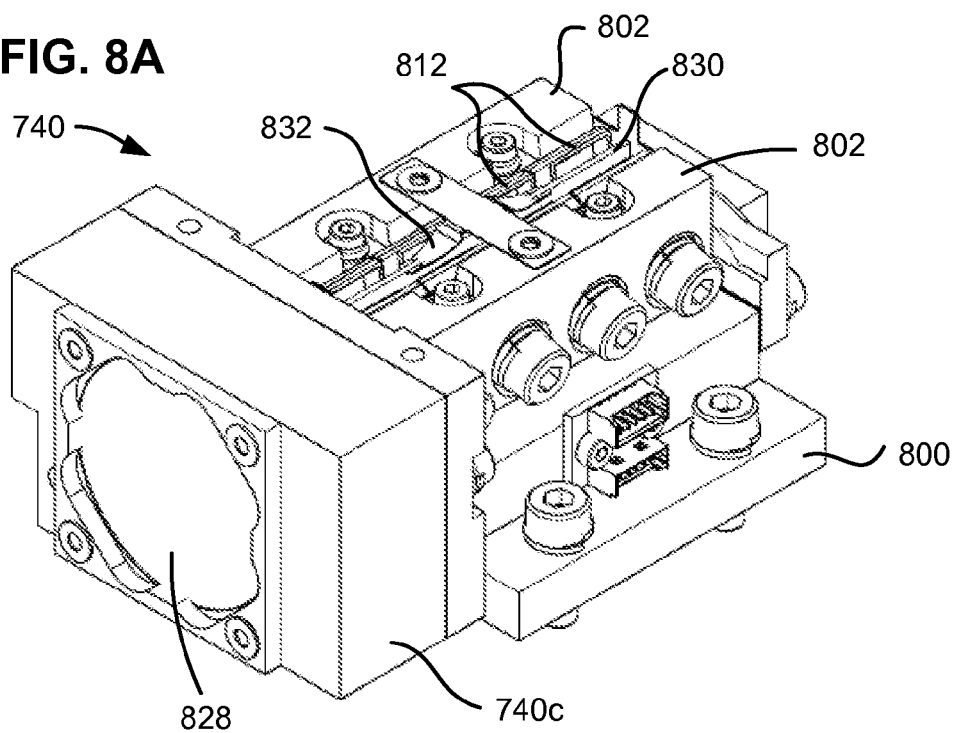
FIG. 8A shows a perspective view of a light pipe engine subsystem of the solid state illumination system of FIGS. 7A to 7E according to an embodiment of the present invention.
Figure 8B:
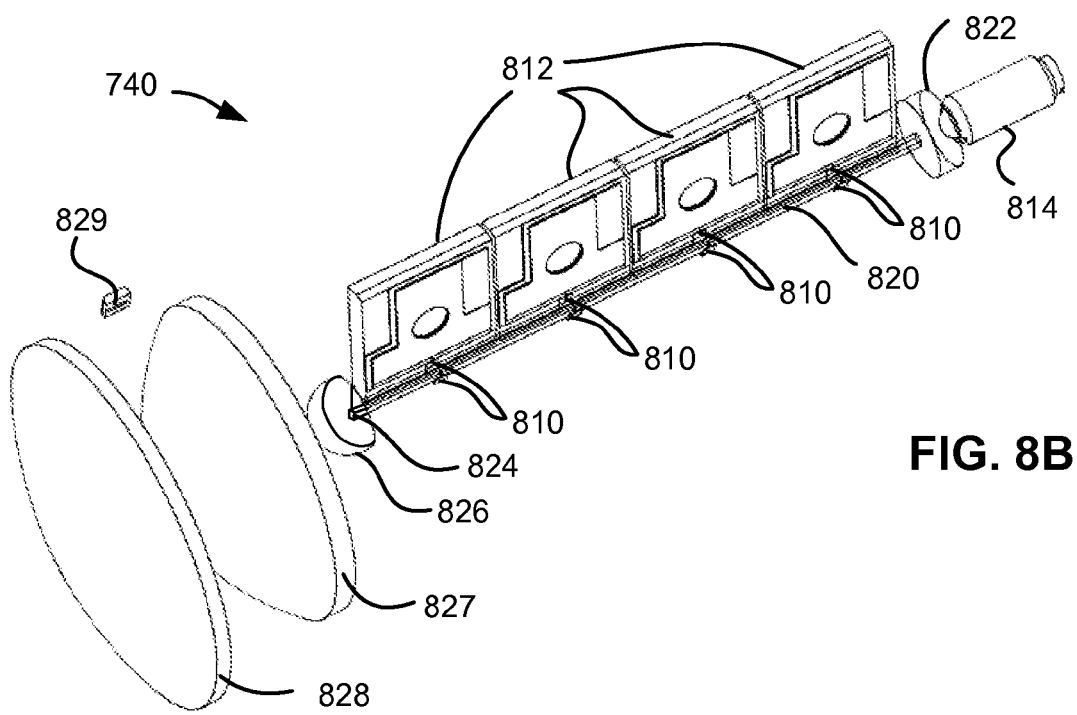
FIG. 8B shows a perspective view of the optical components of the light pipe engine of FIG. 8A.
Figure 8C:
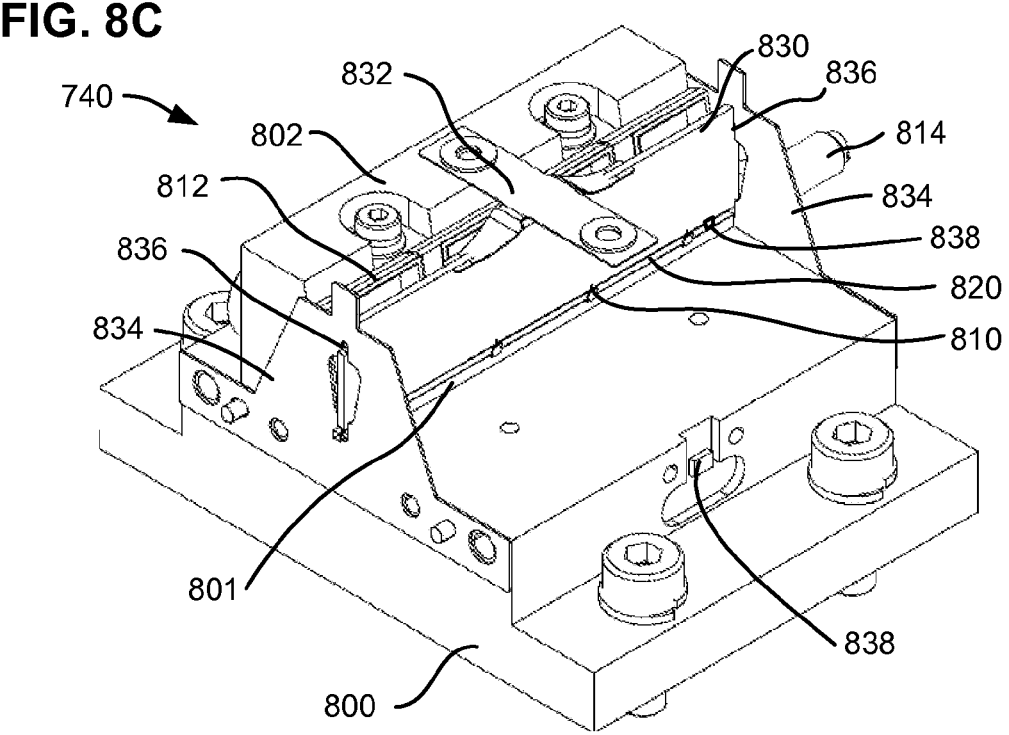
FIG. 8C shows a partial perspective view of the light pipe engine of FIG. 8A.
Figure 8D:
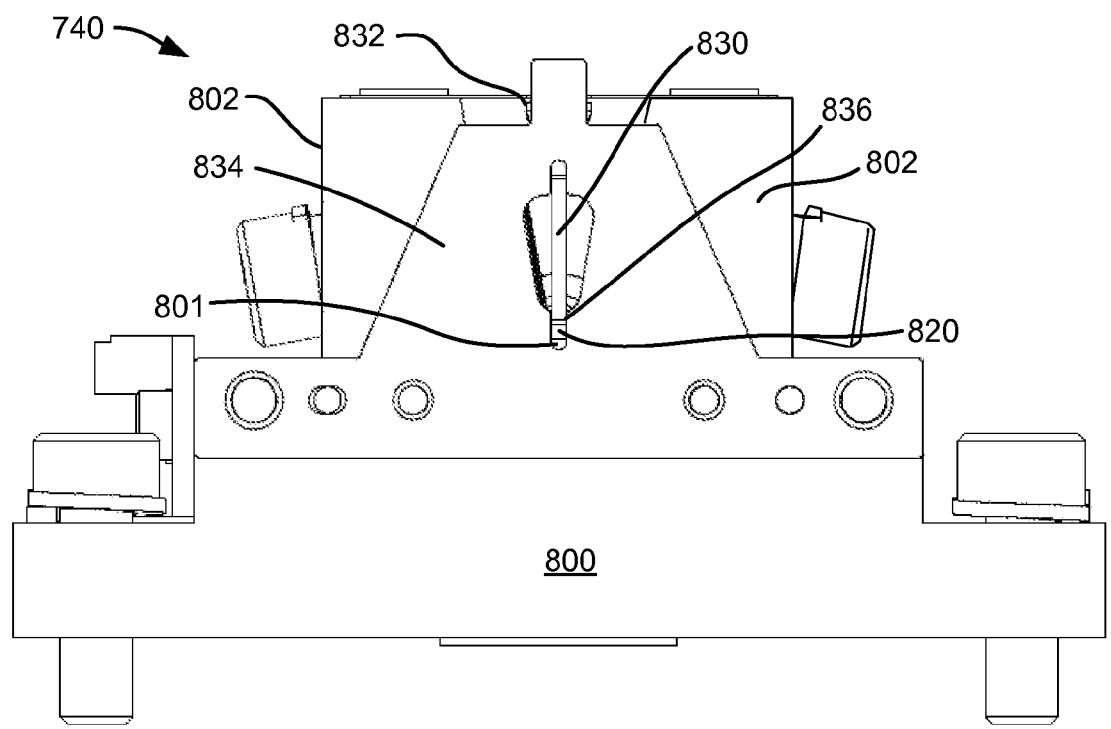
FIG. 8D shows a partial end view of the light pipe engine of FIG. 8A.
Figure 8E:
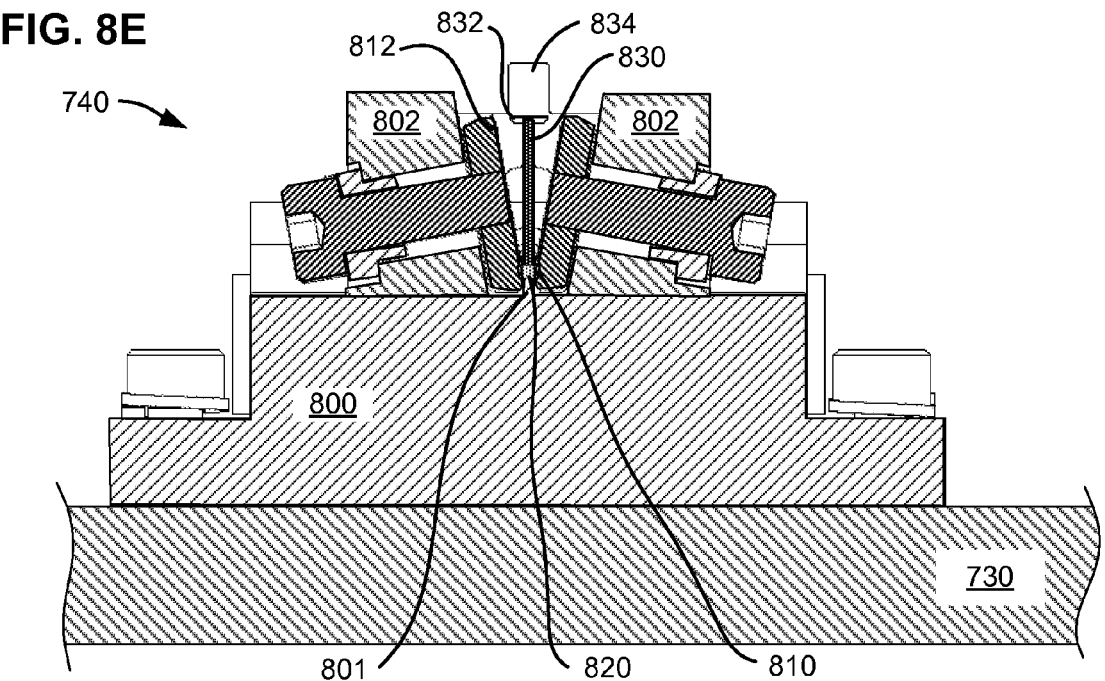
FIGS. 8E and 8F show different sectional views of the light pipe engine of FIG. 8A.
Figure 8F:
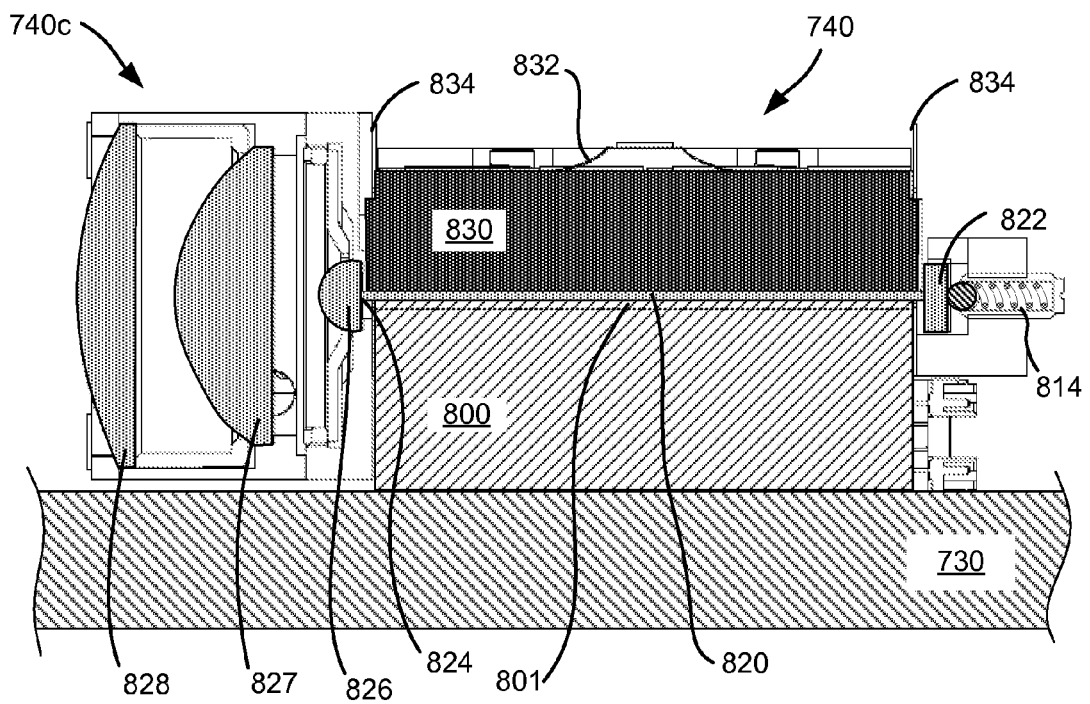

FIGS. 8A-8F show views of light pipe engine 740 of FIG. 7C. FIG. 8A shows a perspective view of light pipe engine 740. FIG. 8B shows a partial perspective view of light pipe engine 740 illustrating the optical components of light pipe engine 740. FIG. 8C shows a partial perspective view of light pipe engine 740 illustrating the arrangement of heat generating components of light pipe engine 740. FIG. 8D shows an end view of components of light pipe engine 740. FIGS. 8E and 8F are sectional views of light pipe engine 740.

Referring first to FIG. 8A which shows a perspective view of light pipe engine 740. Light pipe engine 740 includes base 800 and two slant blocks 802 mounted to base 800. Slant blocks 802 and base 800 are made of a conductive metal or metal alloy. Collimator 740c is mounted to base 800.

FIG. 8B shows a partial perspective view of light pipe engine 740 illustrating the optical components of light pipe engine 740. As shown in FIG. 8B, eight (8) LED dies 810 are arranged in two linear arrays of four (4) along two sides of a luminescent rod 820. Each LED die 810 includes one or more light-emitting diodes. Each LED die 810 is supported by an LED board 812 (only four are shown). At the rear end of luminescent rod 820 and in contact with the end of luminescent rod 820 is a first surface mirror 822. The mirror reflects light toward exit aperture 824 at the front end of luminescent rod 820. A truncated sphere lens 826 is mounted to luminescent rod 820 over exit aperture 824 using optical cement. The mirror 822 is held in contact with luminescent rod 820 by a spring plunger 814. The spring plunger 814 holds mirror 822 against luminescent rod 820 and luminescent rod 820 against truncated sphere lens 826 while accommodating thermal expansion of luminescent rod 820 during operation. Light emitted by luminescent rod 820 is directed by truncated sphere lens 826 to two plano-convex lenses 827, 828 of collimator 740c which operate to collimate the light into a collimated beam. A light sensor 829 is positioned adjacent the periphery of plano-convex lens 827 to monitor light output by luminescent rod 820.

In a preferred embodiment light pipe engine 740 is used to generate green (green and yellow) light spanning 500-600 nm. LED lights that directly emit green light at high power are notoriously difficult to create—the so-called green gap. Thus light pipe engine 740 utilizes high power blue LED light sources to excite a luminescent rod 820 which emits green light spanning 500-600 nm. In a preferred embodiment light pipe engine 740 utilizes two linear arrays of LED dies including forty light emitting diodes to excite emission of green light from the luminescent rod 820. Additional light pipe engines are also described in the Related Applications listed above and incorporated herein by reference. The luminescent rod 820 of the light pipe engine 740 requires cooling during operation and can be convectively cooled as previously described or conductively cooled by being clamped into contact with a metal pedestal heat sink (for example a copper/aluminum/steel heat sink). For example luminescent rod 820 can reach 200° C. during operation as a result of heating by the LEDs and also the stokes energy released during the absorption of blue light and emission of green light. Light pipe engine 740 operating to generate green light allows the solid state illumination system 700 to produce an output in the green and amber bands that is the same or greater than commonly used arc lamps (see, e.g. FIG. 6C). Thus, no compromise in output power, even for the 546 nm band of the arc lamp, is incurred as a consequence of using solid state light illumination system 700 as a replacement for an arc lamp. For example, in an embodiment the optical power of light pipe engine is 3.0 Watts over a range of wavelengths between 500 and 615 nm.

FIG. 8C shows a partial perspective view of light pipe engine 740 illustrating the arrangement of heat generating components of light pipe engine 740. As shown in FIG. 8C, luminescent rod 820 is positioned on a spine 801 which protrudes from base 800. In a preferred embodiment base 800 including spine 801 are made of copper. Spine 801 is roughened where it contacts luminescent rod 820. Spine 801 extends the full length of base 800 and is slightly narrower in width than luminescent rod 820. Luminescent rod 820 is held in contact with spine 801 by ceramic fin 830. Down force is applied to ceramic fin 830 by leaf spring 832 which is mounted between the slant blocks 802 (only one slant block is shown). The down force serves to secure luminescent rod 820 in contact with spine 801. Ceramic fin 830 and luminescent rod 820 are aligned with each other and with spine 801 by slots 836 in end plates 834 mounted to base 800. Slots 836 are preferably laser cut in steel.

As shown in FIG. 8C, LED dies 810 are mounted to LED board 812 (four shown) are secured to slant blocks 802 (one shown) using bolts. In a preferred embodiment each LED board 812 includes 10 light-emitting diodes. Heat generated in LED dies 810 is transmitted through LED boards 812 to slant blocks 802 and thence to base 800. Heat absorbed and/or generated in luminescent rod 820 is transmitted directly to base 800 through spine 801. Thermal sensors 838 are provided on base 800, luminescent rod 820 and LED boards 812 to monitor the temperature of the components during operation. Thus heat generated in the electrical and optical components of light pipe engine 740 is rapidly transmitted to base 800. Base 800 is secured in thermal contact with platform 730 such that heat is rapidly transferred to platform 730 and then dissipated from fins 736 to the cooling air provided by fans 714 (see FIGS. 7C and 7D). In a preferred embodiment platform 730 is made in one piece from aluminum.

FIG. 8D shows an end view of light pipe engine 740 illustrating alignment of ceramic fin 830 and luminescent rod 820 with spine 801 of base 100 by slot 836 in end plate 834. Luminescent rod 820 is held in contact with spine 801 by ceramic fin 830. Down force is applied to ceramic fin 830 by leaf spring 832 which is mounted between the slant blocks 802. The down force serves to secure luminescent rod 820 in contact with spine 801. Ceramic fin 830 and luminescent rod 820 are aligned with each other and with spine 801 by slots 836 in end plates 834 mounted to base 800. Slots 836 are preferably laser cut in steel.

FIG. 8E shows a sectional view of light pipe engine 740 perpendicular to the axis of luminescent rod 820. FIG. 8F shows a sectional view of light pipe engine 740 parallel to the axis of luminescent rod 820. FIGS. 8E and 8F illustrate the cooperation between the components of light pipe engine 740 to maintain luminescent rod 820 and the LED boards 812 in close thermal contact with slant blocks 802 and base 800. FIG. 8F also illustrates the optical path including mirror 822, luminescent rod 820, truncated sphere lens 826 and plano-convex lenses 827 and 828.

Figure 9A:
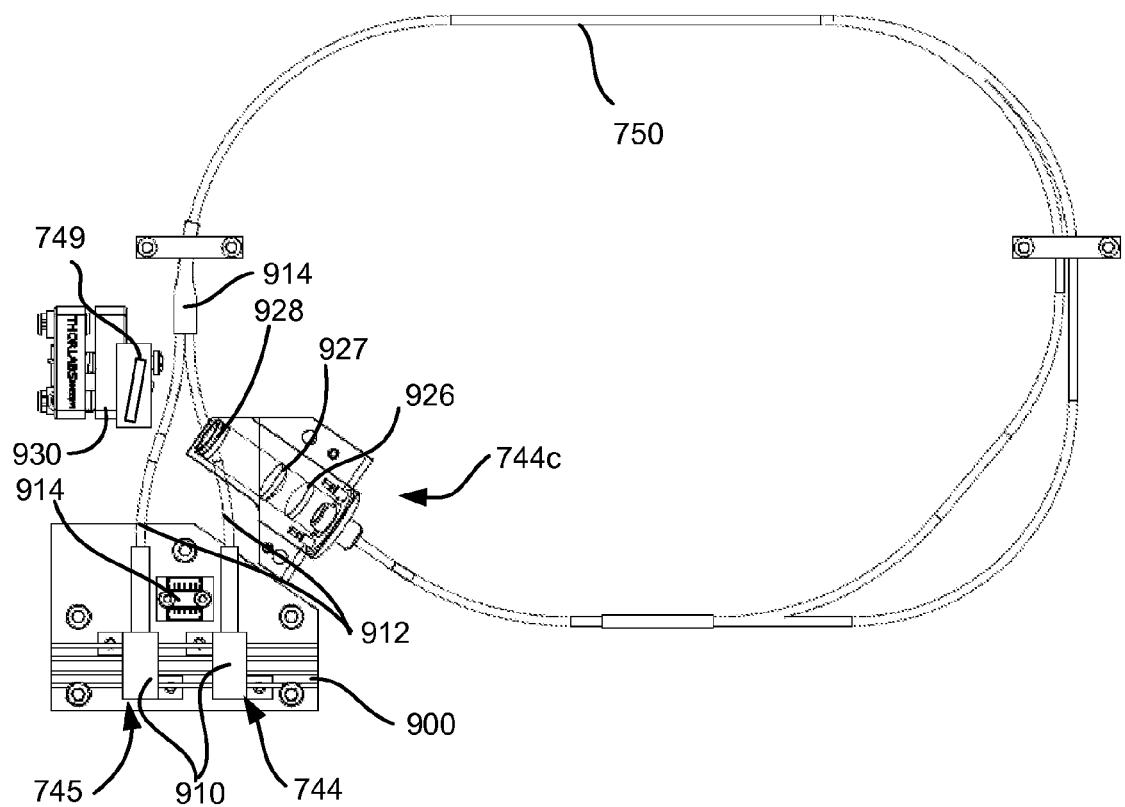
FIG. 9A shows a top view of a laser light subsystem of the solid state illumination system of FIGS. 7A to 7E according to an embodiment of the present invention.
Figure 9B:
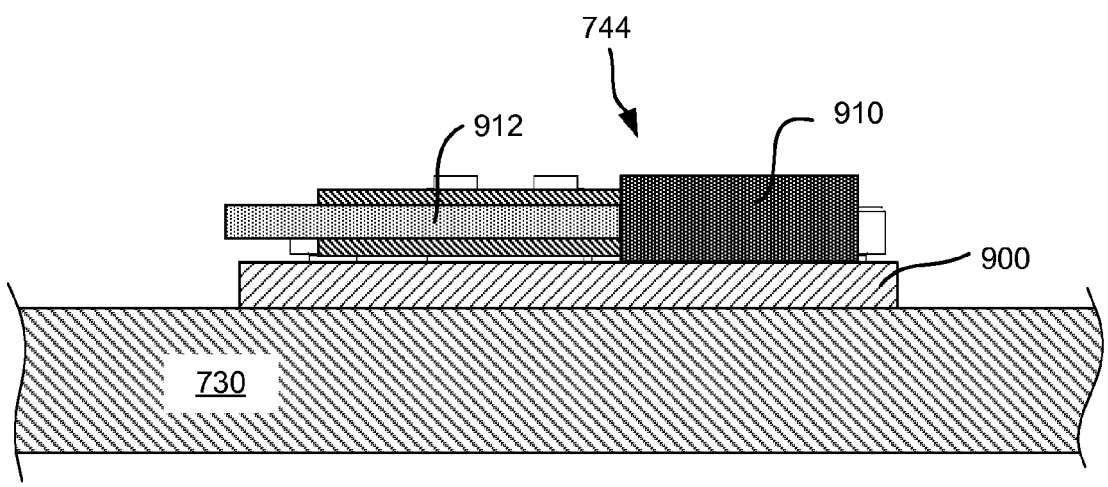
FIG. 9B shows a sectional view of a laser light subsystem of FIG. 9A.

FIGS. 9A and 9B illustrate the two solid state laser light sources 744, 745 and related collimator 744c and optical fiber 750. As shown in FIG. 9A, laser light sources 744, 745 each include a laser-diode module 910, coupled to an optical fiber 912. The laser-diode modules emit coherent light of a selected narrow wavelength. For example laser-diode modules in an embodiment emit coherent near-IR light. A connector 914 links the two optical fibers 912 into an optical fiber 750 which connects to collimator 744c. Optical fiber 750 serves to mix and homogenize the coherent light from laser light sources 744, 745 reducing artifacts such as speckling and interference fringing in the light. The combined coherent light exits optical fiber 750 into collimator 744c which includes three plano-convex lenses 926, 927 and 928. Collimator 744c also serves to expand the laser light from laser light sources 744, 745. The first plano-convex lens 926 is arranged to expand the light beam exiting the optical fiber 750. The second and third plano-convex lenses 927, 928 collimate the expanded beam and direct the expanded beam of coherent light at first-surface mirror 749. First surface mirror 749 is aligned such that the expanded beam of coherent light is directed along optical axis 752 towards output optics 756 (see FIG. 7E). An adjustable mount 930 facilitates alignment of first-surface mirror 749.

As shown in FIGS. 9A and 9B laser diode modules 910 are mounted to a base 900. Base 900 is a conductive metal base which is itself mounted in thermal contact with platform 730. Heat created by the operation of laser diode modules 910 is transmitted to base 900 and thence to platform 730 where it is dissipated from fins 736 to the cooling air provided by fans 714 (see FIGS. 7C and 7D). One or more thermal sensors are provided to monitor the temperature of laser diode modules 910 and/or base 900 during operation.

Figure 10C:
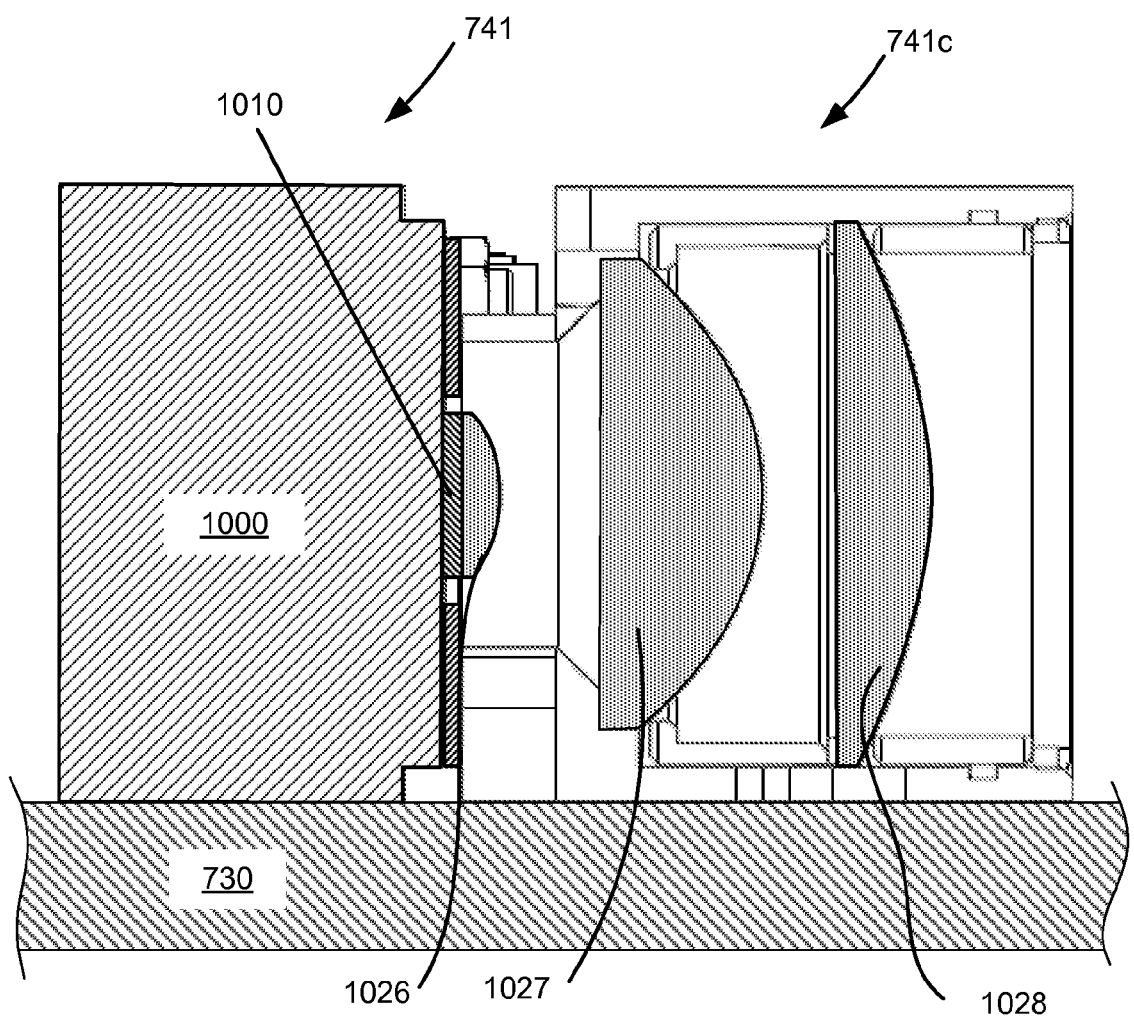
FIG. 10C shows a sectional view of the LED light source subsystem of FIG. 10A.

FIGS. 10A-10C shows views of LED light source 741. LED light sources 742 and 743 have the same design though each of LED light sources 741, 742 and 743 preferably includes LEDs which emit light of different wavelengths than the others of LED light sources 741, 742 and 743. FIG. 10A shows a perspective view of LED light source 741, collimator 741c and associated dichroic mirror 748. As shown in FIG. 10A, Led light source 741 includes a base 1000 adapted to be mounted to platform 730 (see FIGS. 7C-7E). Collimator 741c is mounted to base 1000.

FIG. 10B shows a partial perspective view of LED light source 741, collimator 741c and associated dichroic mirror 748. As shown in FIG. 10B, LED light source 741 includes an LED die 1010. LED die 1010 includes a plurality of light-emitting diodes on the same substrate. The substrate is mounted in direct or indirect thermal contact with base 1000 such that heat generated by the light-emitting diodes during operation is transmitted to base 1000. Base 1000 is secured in thermal contact with platform 730 such that heat is rapidly transferred to platform 730 and then dissipated from fins 736 to the cooling air provided by fans 714 (see FIGS. 7C and 7D).

Referring again to FIG. 10B, light emitted from LED die 1010 is collected through plano-convex-lens 1026 placed over die 1010. The light passes through plano-convex lens 1026 and is collimated by plano-convex lenses 1027, 1028 of collimator 741c. A light sensor 1029 is placed adjacent plano-convex lens 1027 where it receives scattered light in order to monitor the light output of LED die 1010. After passing plano-convex lenses 1027, 1028 the collimated light beam is directed at dichroic mirror 748. Dichroic mirror 748 is aligned such that the collimated beam of light is directed along optical axis 752 towards output optics 756 (see FIG. 7E).

FIG. 10C shows a sectional view of LED light source 741 and collimator 741c. As shown in FIG. 10C, LED light source 741 includes an LED die 1010. LED die 1010 includes a plurality of light-emitting diodes on the same substrate. The substrate is mounted in direct or indirect thermal contact with base 1000 such that heat generated by the light-emitting diodes of LED die 1010 during operation is transmitted to base 1000. Base 1000 is secured in thermal contact with platform 730 such that heat is rapidly transferred to platform 730 and then dissipated from fins 736 to the cooling air provided by fans 714 (not shown, but see FIGS. 7C and 7D). Referring again to FIG. 10C, light emitted from LED die 1010 is collected through plano-convex-lens 1026 placed over die 1010. The light passes through plano-convex lens 1026 and is collimated by plano-convex lenses 1027, 1028 of collimator 741c.

Figure 11C:
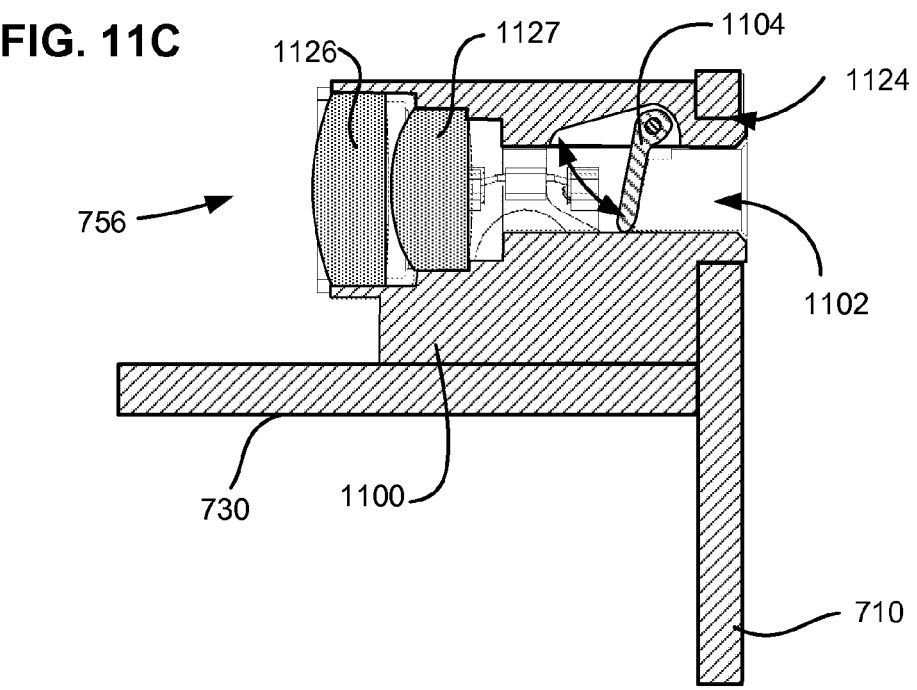
FIGS. 11C and 11D show different sectional views of the output optics subsystem of FIG. 11A.

FIGS. 11A-11D illustrate output optics 756 of solid state illumination system 700 (see FIGS. 7C and 7E). As shown in FIG. 11A, output optics 756 receives the collimated combined beam of light 754 from all the light sources of solid state illumination system 700, focuses the combined beam 754 and directs it into the aperture 1128 of light guide 706. An adapter 716 connects light guide 706 to output optics 756 and positions light guide 706 such that the aperture of the light guide is correctly positioned to receive the focused combined beam of light. Output optics 756 are positioned against front plate 710 such that light guide 706 can be connected to output optics 756 through an aperture in front plate 710.

As shown in FIG. 11B, output optics 756 includes two plano-convex lenses 1126, 1127. Plano-convex lenses 1126, 1127 receive the collimated combined beam of light 754 from all the light sources of solid state illumination system 700, focuses the combined beam 754 and directs it into the aperture 1128 of light guide 706. Light guide 706 transmits the combined beam to an optical instrument such as a microscope or endoscope.

Figure 11D:
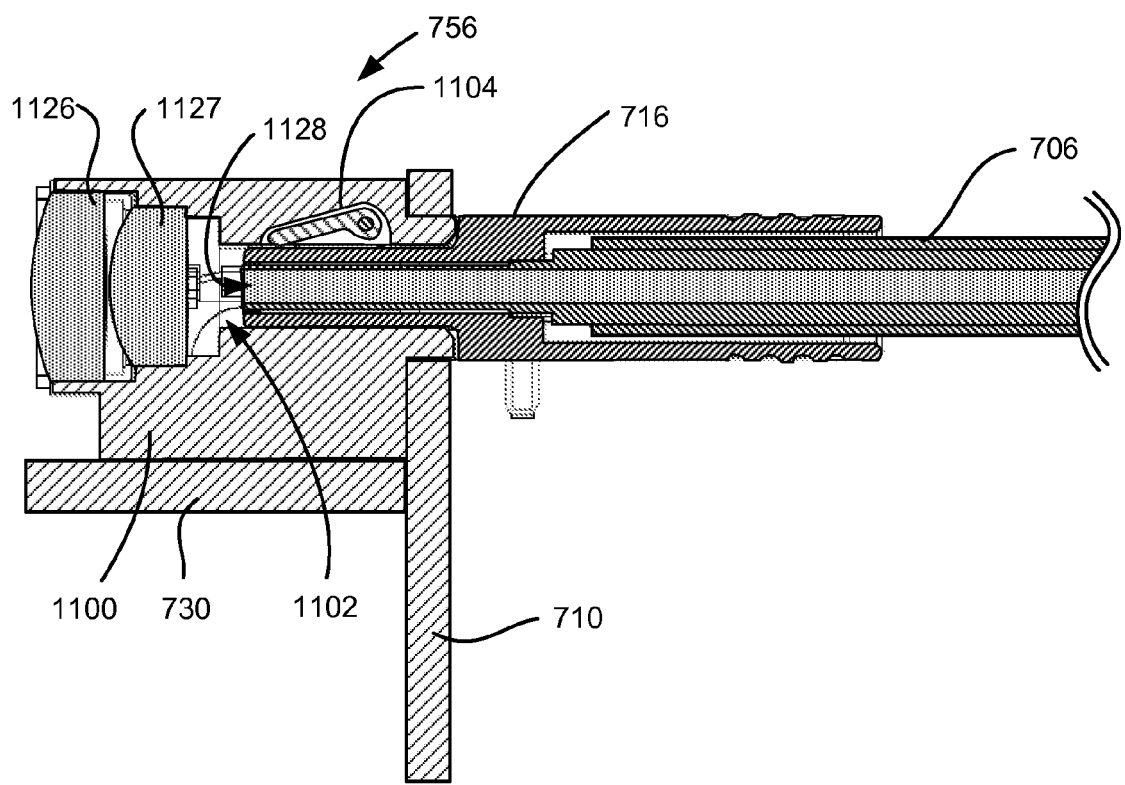

FIGS. 11C and 11D are sectional views of output optics 756 illustrating attachment of a light guide 706. FIG. 11C shows output optics without light guide 706 in place. As shown in FIG. 11C, light guide 706 includes a housing 1100 which defines a lumen 1102. Housing 1100 is mounted to platform 730. Housing 1100 projects through aperture 1124 in front plate 710 such that lumen 1102 is accessible from the exterior of solid state illumination system 700. As shown in FIG. 11C, a safety flap 1104 occludes lumen 1102 to prevent the exit of light or entry of contaminants through lumen 1102 when light guide 706 is not connected. Safety flap 1104 is spring loaded such that it occludes lumen 1102 automatically upon removal of a light guide 706. Safety flap 1104 pivots out of the way when a light guide 706 is inserted. One or more limit sensors (not shown) are coupled to safety flap 1104 to sense the position of safety flap 1104 (and thus the presence or absence of a light guide) and provide such information to controller board 738.

As shown in FIG. 11D, light guide 706 is received in an adapter 716 which connects light guide 706 to output optics 756 and positions light guide 706 such that the aperture 1128 of the light guide 706 is correctly positioned to receive the focused combined beam of light. When adapter 716 and light guide 706 are inserted into lumen 1102 of housing 1100, safety flap 1104 pivots out of the way. Aperture 1128 is positioned coaxial with plano-convex lenses 1126, 1127 such that the combined beam of light is focused into aperture 1128 of light guide 706. Light guide 706 transmits the combined beam to an optical instrument such as a microscope or endoscope.

The illuminations systems and components thereof described herein may, with suitable adaptation, find application in a range of applications including: life science applications which cover a range of white light and/or fluorescence analyses and quantitation; microscopy; fluorescence microscopy; high content screening; genetic expression analysis; digital pathology; and endoscopy.

Other features, aspects and objects of the invention can be obtained from a review of the figures and the claims. It is to be understood that other embodiments of the invention can be developed and fall within the spirit and scope of the invention and claims.

What is claimed is:

1. A light source comprising:
a rod comprising a luminescent material;
the rod having a first end opposite a second end, an elongated top surface opposite an elongated bottom surface, and first and second side surfaces disposed between the elongated top surface and the elongated bottom surface;
a metal base having a raised spine having a contact surface adapted to contact substantially all of the elongated bottom surface of the rod;
a fin having a first fin end, a second fin end, and an edge adapted to contact substantially all of the elongated top surface of the rod;
a spring configured and positioned to apply a force to said fin to push the edge against the elongated top surface of the rod whereby the elongated bottom surface of the rod is held in thermal contact with the contact surface of the spine of the metal base;
a plurality of light emitting diodes which emit first light of a first color;
the plurality of light emitting diodes positioned adjacent the first and second side surfaces of the rod such that the first light of a first color enters the rod through the first and second side surfaces and is absorbed by the luminescent material which in response emits by fluorescence second light of a second color different than the first color which second light is transmitted along said rod to said first end and second end; and
wherein the rod is temperature regulated by transmission of heat from the rod to the spine of the metal base.

2. The light source of claim 1, further comprising:
a first end plate mounted to the base, the first end plate having a first slot aligned with the spine;
wherein the first end of the rod is received through said first slot such that the rod is aligned with the spine by said first end plate.

3. The light source of claim 2, further comprising:
a second end plate mounted to the base, the second end plate having a second slot aligned with the spine;
wherein the second end of the rod is received through said second slot such that the rod is aligned with the spine by said second end plate.

4. The light source of claim 1, further comprising:
a first end plate mounted to the base, the first end plate having a first slot aligned with the spine;
wherein the first end of the rod and the first fin end of the fin are received through said first slot such that the fin is aligned with the rod and the rod is aligned with the spine by said first end plate.

5. The light source of claim 4, further comprising:
a second end plate mounted to the base, the second end plate having a second slot aligned with the spine;
wherein the second end of the rod and the second fin end of the fin are received through said second slot such that the fin is aligned with the rod and the rod is aligned with the spine by said second end plate.

6. The light source of claim 1, further comprising:
a temperature sensor mounted in thermal contact with the base to monitor the temperature of the base.

7. The light source of claim 1, further comprising a heat sink mounted to said base.

8. The light source of claim 1, further comprising a fan for cooling the base.

9. The light source of claim 1, further comprising a mirror coupled to the second end of the rod to reflect the second light towards the first end of the rod.

10. The light source of claim 9, further comprising a spring which resiliently holds the mirror against the second end of the rod to accommodate thermal expansion of the rod.

11. A light source comprising:
a rod comprising a luminescent material;
the rod having a first end opposite a second end, an elongated top surface opposite an elongated bottom surface, and first and second side surfaces disposed between the elongated top surface and the elongated bottom surface;
a plurality of light emitting diodes which emit first light of a first color, the plurality of light emitting diodes positioned adjacent at least one of the first and second side surfaces of the rod such that the first light of a first color enters the rod through at least one of the first and second side surfaces and is absorbed by the luminescent material which in response emits by fluorescence second light of a second color different than the first color which second light is transmitted along said rod to said first end and second end;
a metal base including a raised spine having a contact surface adapted to contact substantially all of the elongated bottom surface of the rod;
a substantially planar fin having a first fin end, a second fin end, and an edge adapted to contact the elongated top surface of the rod; and
a spring configured and positioned to apply a force to said fin to push the edge against the elongated top surface of the rod whereby the elongated bottom surface of the rod is held against the contact surface of the spine of the metal base such that the rod temperature is regulated by transmission of heat from the rod to the spine of the metal base.

12. The light source of claim 11, further comprising:

a first end plate mounted to the base, the first end plate having a first slot aligned with the spine;

wherein the first end of the rod is received through said first slot such that the rod is aligned with the spine by said first end plate.

13. The light source of claim 12, further comprising:

a second end plate mounted to the base, the second end plate having a second slot aligned with the spine;

wherein the second end of the rod is received through said second slot such that the rod is aligned with the spine by said second end plate.

14. The light source of claim 11, further comprising:

a first end plate mounted to the base, the first end plate having a first slot aligned with the spine;

wherein the first end of the rod and the first fin end of the fin are received through said first slot such that the fin is aligned with the rod and the rod is aligned with the spine by said first end plate.

15. The light source of claim 14, further comprising:

a second end plate mounted to the base, the second end plate having a second slot aligned with the spine;

wherein the second end of the rod and the second fin end of the fin are received through said second slot such that the fin is aligned with the rod and the rod is aligned with the spine by said second end plate.

16. The light source of claim 11, further comprising:

a temperature sensor mounted in thermal contact with the base to monitor the temperature of the base.

17. The light source of claim 11, further comprising a heat sink mounted to said base.

18. The light source of claim 11, further comprising a fan for cooling the base.

19. The light source of claim 11, further comprising a mirror coupled to the second end of the rod to reflect the second light towards the first end of the rod.

20. The light source of claim 19, further comprising a spring which resiliently holds the mirror against the second end of the rod to accommodate thermal expansion of the rod.

* * * * *